US012778586B2

(12) United States Patent
Steinmetz et al.

(10) Patent No.: US 12,778,586 B2
(45) Date of Patent: Nov. 3, 2026

(54) METHOD OF MAKING SUTURELESS ANASTOMOSIS FOR FLUID COUPLING TO ANATOMICAL STRUCTURES

(71) Applicant: ConneX Biomedical, Inc., Aurora, CO (US)

(72) Inventors: Jeffrey N. Steinmetz, Arvada, CO (US); Jeremy N. Morgan, Missoula, CO (US)

(73) Assignee: ConneX Biomedical, Inc., Aurora, CO (US)

( * ) Notice: Subject to any disclaimer, the term of this patent is extended or adjusted under 35 U.S.C. 154(b) by 62 days.

(21) Appl. No.: 19/054,771

(22) Filed: Feb. 14, 2025

(65) Prior Publication Data

US 2025/0318834 A1 Oct. 16, 2025

Related U.S. Application Data

(60) Provisional application No. 63/554,871, filed on Feb. 16, 2024.

(51) Int. Cl.

| | |
|---|---|
| ***A61B 17/11*** | (2006.01) |
| ***A61B 17/00*** | (2006.01) |
| ***A61F 2/06*** | (2013.01) |

(52) U.S. Cl.

CPC ................ *A61B 17/11* (2013.01); *A61F 2/06* (2013.01); *A61B 2017/00477* (2013.01); *A61B 2017/00867* (2013.01); *A61B 2017/1107* (2013.01); *A61B 2017/1132* (2013.01); *A61B 2017/1135* (2013.01); *A61F 2220/0016* (2013.01)

(58) Field of Classification Search

CPC ... A61B 17/064; A61B 17/0644; A61B 17/11; A61B 2017/00477; A61B 2017/00867; A61B 2017/0641; A61B 2017/1107; A61B 2017/1132; A61B 2017/1135; A61F 2/06; A61F 2220/0016

See application file for complete search history.

(56) References Cited

U.S. PATENT DOCUMENTS 5,797,933 A * 8/1998 Snow ............... A61B 17/12109 606/198

7,022,131 B1 * 4/2006 Derowe ........... A61B 17/22012 623/1.11

* cited by examiner

*Primary Examiner* — Mohamed G Gabr

(74) *Attorney, Agent, or Firm* — Rosenbaum IP, P.C.; David G. Rosenbaum

(57) ABSTRACT

Connectors for end-to-end and/or end-to-side coupling of either anatomical tissue to other anatomical tissue and/or non-anatomical devices to anatomical tissue. The connectors and their variants are each characterized by having at least one mechanically active tine that are actuated by extension or compression of a mechanical mechanism linking the active tines to a frame. The mechanical mechanism may actuate by one or more of shape memory, superelastic, elastic deformation, plastic deformation, electromechanical and/or other motive mechanism operably associated with the at least one mechanically active tines and the frame to rotate the tines about a hinge region under the influence of the mechanical mechanism.

14 Claims, 18 Drawing Sheets

METHOD OF MAKING SUTURELESS ANASTOMOSIS FOR FLUID COUPLING TO ANATOMICAL STRUCTURES

CROSS-REFERENCE TO RELATED APPLICATIONS

This application is related to and claims priority to U.S. Provisional patent application Ser. No. 63/554,871, filed Feb. 16, 2024. This application is also related to co-pending U.S. patent application Ser. No. 18/458,398, filed Aug. 30, 2023, which is hereby incorporated by reference in its entirety.

BACKGROUND OF THE DISCLOSURE

The present disclosure pertains generally to sutureless connectors for coupling with anatomical tissue. More particularly, the present disclosure pertains to connectors for end-to-end and/or end-to-side coupling of either anatomical tissue to other anatomical tissue and/or non-anatomical devices to anatomical tissue. The connectors of the present disclosure are each characterized by having at least one mechanically active tines that are actuated by extension or compression of a mechanical mechanism linking the active tines to a frame. The mechanical mechanism may actuate by one or more of the following properties: shape memory, superelastic, elastic deformation, plastic deformation, electromechanical and/or other mechanical mechanism operably associated with the at least one mechanically active tines and the frame.

The at least one mechanically active tines are generally elongated members, optionally, having a taper along their longitudinal axis to a distal point to facilitate penetration into anatomic tissue. Each of the at least one mechanically active tines are coupled to a mechanism that is adapted to either extend or compress the at least one mechanically active tines without employing an anvil. Rather, the mechanism that is adapted to either extend or compress the at least one mechanically active tines consists generally of a support frame, at least one actuating member, and at least one tine projecting from the actuating member.

The support frame may be configured as a planar frame, a linear frame, a ring frame, an undulating frame, or a plurality of arcuate frame members adapted to form a ring. The at least one actuating member is coupled to the support frame and movable in a substantially co-planar relationship relative to the support frame. The at least one mechanically active tine is coupled to both the support frame and the at least one actuating member. The at least one mechanically active tine is configured to move in an opposite direction from movement of the at least one actuating member, e.g., the at least one mechanically active tine will move proximally as the at least one actuating member is moved distally and to move distally as the at least one actuating member is moved proximally.

Where plural mechanically active tines are provided with a common support frame, plural actuating members will also be provided with an actuating member coupled with a mechanically active tine. The plural actuating members and the plural mechanically active tines may be actuated individually or simultaneously by either axial compression or expansion of the plural actuating members.

Each actuating member, mechanically active tine coupled thereto, support frame, and associated elements, such as stabilizing members, expansive members, tension members, compression members, as hereinafter described, define a tine assembly and plural tine assemblies may be provided on a common individual support frame or on plural support frames.

In accordance with one aspect of the present disclosure, where plural mechanically active tines are employed, the mechanically active tines have a length configured such that when the mechanically active tines are fully deployed, the anatomic tissue and/or non-anatomic device is compressed between the mechanically active tine and its associated actuating member without substantial regions of uncompressed anatomic tissue and/or non-anatomic device. This results from the length of each mechanically active tine being configured to spatially abut or be spatially adjacent to another, immediately adjacent, mechanically active tine.

Those skilled in the art will appreciate that the sutureless connector of the present disclosure functions in a manner similar to a surgical staple, however, without the necessity of an anvil to deform legs of the surgical stable. Moreover, where plural actuating members and plural mechanically active tines are provided on a common frame, each support frame carries a plurality of plural actuating members and plural mechanically active tines.

SUMMARY OF THE DISCLOSURE

It is an object of the present disclosure to provide a sutureless connector for coupling to anatomic tissue to facilitate end-to-end or end-to-side connections between anatomic tissue and/or between anatomic tissue and other non-anatomical devices.

It is a further object of the present disclosure to provide a sutureless connector for coupling to anatomic tissue that includes a frame and at least one of a plurality of mechanically tine assemblies arrayed in series on the frame.

It is another object of the present disclosure to provide a sutureless connector having at least one mechanically active tine that is adapted to allow the at least one mechanically active tine to penetrate into anatomic tissue and/or non-anatomic devices and, upon actuation of the sutureless connector to compress the at least one mechanically active tine against the anatomic tissue and/or non-anatomic device such that a portion of the anatomic tissue and/or non-anatomic device is compressed between the at least one mechanically active tine and the at least one actuating member and/or support frame of the sutureless connector.

It is a further object of the present disclosure to provide a sutureless connector having at least one mechanically active tine that is adapted to allow the at least one mechanically tine to penetrate into anatomic tissue and/or non-anatomic devices and, upon actuation of the sutureless connector to decompress the at least one mechanically active tine away from the anatomic tissue and/or non-anatomic device such that a portion of the anatomic tissue and/or non-anatomic device is released from the at least one mechanically active tine.

It is yet another object of the present disclosure to provide a sutureless connector having a frame, at least one mechanically active tine, and an actuation mechanism coupled to the frame and to the at least one mechanically active tine.

It is still another object of the present disclosure to provide a frame that is planar, curved, arcuate, or a ring structure.

It is yet another further object of the present disclosure to provide at least one mechanically active tine that is linear or arcuate and, optionally, has a taper along its longitudinal axis.

It is still another further object of the present disclosure to provide the at least one mechanically active tine with a hinge region at or proximate to a junction between a proximal end of the at least one mechanically active tine and the frame and the actuation mechanism.

It is still yet another object of the present disclosure that the frame further include a projection that joins with the hinge region of the at least one mechanically active tine.

It is a further object of the present disclosure that the projection from the frame is configured to bear a compression force upon extension of the at least one actuating member relative to the frame member and a tension force upon contraction of the at least one actuating member relative to the frame member.

It is still another object of the present disclosure that the projection from the frame is configured to bear a tension force upon extension of the at least one actuating member relative to the frame member and a compression force upon contraction of the at least one actuating member relative to the frame member.

It is still a further objective of the present disclosure that the actuating member have a projection that is configured to bear a compression force upon extension of the at least one actuating member and a tension force upon contraction of the at least one actuating member relative to the frame member.

These and other objects, features, and advantages of the present disclosure will be more apparent to those skilled in the art from the following more detailed description of the disclosure and its variants taken with reference to the accompanying figures.

DETAILED DESCRIPTION

Figure 1A:
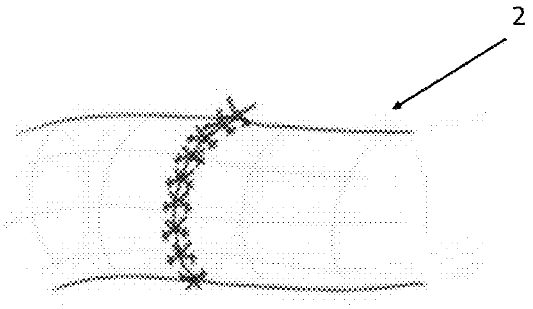
(Prior Art) FIG. 1A
FIG. 1A is a perspective view of an end-to-end anastomosis of two anatomical lumen tissues in accordance with the prior art.

For purposes of clarity, the following terms used in this patent application will have the following meanings:

The terminology used herein is for the purpose of describing example variants only and is not intended to be limiting. As used herein, the singular forms "a." "an," and "the" may be intended to include the plural forms as well, unless the context clearly indicates otherwise. The terms "comprises." "comprising." "including." and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the order discussed or illustrated, unless specifically identified as an order of performance. It is also to be understood that additional or alternative steps may be employed When an element or layer is referred to as being "on," "engaged," "connected," or "coupled" to or with another element, it may be directly on, engaged, connected, or coupled to the other element or layer, or intervening elements or layers may be present. In contrast, when an element is referred to as being "directly on," "directly engaged to," "directly connected to," or "directly coupled to" or with another element or layer, there may be no intervening elements or layers present. Other words used to describe the relationship between elements should be interpreted in a like fashion (e.g., "between" versus "directly between," "adjacent" versus "directly adjacent," etc). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may distinguish one element, component, region, layer or section from another region, layer, or section. Terms such as "first," "second," and other numerical terms when used herein do not imply a sequence or order unless clearly indicated by the context. Thus, a first element, component, region, layer, or section discussed below could be termed a second element, component, region, layer, or section without departing from the teachings of the example variants.

Spatially relative terms, such as "inner," "outer," "beneath," "below," "lower," "above," "upper." and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures For example, if the device in the figures is turned over, elements described as "below", or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

"Substantially" is intended to mean a quantity, property, or value that is present to a great or significant extent and less than, more than or equal to total. For example, "substantially vertical" may be less than, greater than, or equal to completely vertical.

"About" is intended to mean a quantity, property, or value that is present at +10%. Throughout this disclosure, the numerical values represent approximate measures or limits to ranges to encompass minor deviations from the given values and variants having about the value mentioned as well as those having the precise value mentioned. Other than in the working examples provided at the end of the detailed description, all numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters. In addition, disclosure of ranges includes disclosure of all values and further divided ranges within the entire range, including endpoints given for the ranges.

The use of the terms "a" and "an" and "the" and similar referents in the context of describing the disclosure are to be construed to cover both the singular and the plural, unless otherwise indicated herein or clearly contradicted by context. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Recitation of ranges of values herein are merely intended to serve as a shorthand method of referring individually to each separate value falling within the recited range, unless otherwise indicated herein, and each separate value is incorporated into the specification as if it were individually recited herein.

References to "variant" or "variant", e.g., "one variant," "an variant," "example variant," "various variants," etc., may indicate that the variant(s) or variant(s) of the disclosure so described may include a particular feature, structure, or characteristic, but not every variant necessarily includes the particular feature, structure, or characteristic. Further, repeated use of the phrase "in one variant," or "in an exemplary variant," do not necessarily refer to the same variant or variant, although they may.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical, and medical arts. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

The terms "configured to" or "adapted to" are used synonymously and are intended to mean that a recited structure is intended to perform a particular recited function or assume a particular recited configuration and is not merely capable thereof.

The terms "proximal" or "distal" are intended to be relative positional references and are used with reference either to a direction of blood flow relative to a device or device component or with reference to a longitudinal axis of a device or device component. For example, with reference to the connector of the present disclosure, the proximal end of the connector refers to a portion of the connector away from the tissue being connected and the distal end of the connector refers to a portion of the connector closest to the tissue being connected.

The term "ring" is intended to refer to a structure or structures that are configured to subtend substantially a 360-degree arc and may be a single continuous structure or plural arcuate structures. A ring may have a circular or non-circular profile, e.g., elliptical, oval, kidney-shaped, or the like.

The term "graft" is intended to refer to any type of tubular structure and may be comprised of polymeric, biological, composite, or metal materials.

The term "anatomic tissue" is intended to refer to any anatomic structure within a mammalian body.

The term "anatomic passageway" is intended to refer to any anatomical structure having a lumen. Examples of anatomic passageways are blood vessels, the gastrointestinal track, including the esophagus, stomach, small intestine, large intestine, and rectum, or airway passages, such as the trachea and bronchi.

The terms "major vessel" and/or "aorta" as used herein reference specific and non-limiting examples of anatomic passageways. It is intended that the terms "anatomic passageway," "major vessel," and/or "aorta" are used interchangeably and synonymously.

The term "flange" is intended to refer to any type of radially extending projection, including, without limitation, a projection that extends less than or equal to 360 degrees relative to the element that the projection extends from. Further, a flange may have a longitudinal component to its projection orientation relative to the element that the projection extends from.

The term "operably coupled" is intended to mean that a first element or elements are coupled to a second element or other elements in a manner in which the first element(s) acts upon the second element(s) to cause the second element(s) to operate, e.g., move, in some defined manner.

The term "mechanically active" is intended to refer to a mechanism by which the at least one tine is either contracted or extended about a longitudinal axis of the at least one tine by virtue of the at least one tine and/or elements cooperating with or acting upon the at least one tine having shape memory, superelastic, elastic, and/or plastic deformation properties.

This detailed description of exemplary variants references the accompanying drawings, which show exemplary variants by way of illustration. While these exemplary variants are described in sufficient detail to enable those skilled in the art to practice the disclosure, it should be understood that other variants may be realized and that logical changes and adaptations in design and construction may be made in accordance with this disclosure and the teachings herein without departing from the spirit and scope of the disclosure. Thus, the detailed description herein is presented for purposes of illustration only and not for purposes of limitation.

Figure 1B:
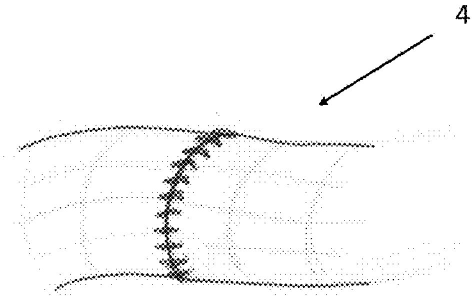
FIG. 1B is a perspective view of an alternative end-to-end anastomosis of two anatomical lumen tissues.
Figure 1C:
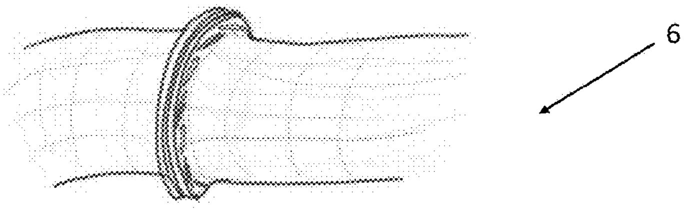
FIG. 1C is a perspective view of another alternative end-to-end anastomosis of two anatomical lumen tissues.

Turning now to the accompanying Figures in which there are illustrated exemplary variants of the connector of the present disclosure. FIG. 1A depicts a conventional method of a sutured end-to-end anastomosis of two anatomical vessels. Such sutured anastomosis is typically conducted with one or more continuous uninterrupted suture(s) about the circumference of both anatomical vessels being coupled. As shown in FIG. 1B and FIG. 1C, the connector 100 of the present disclosure, together with its variants, is suitable for use in an end-to-end anastomosis 4 or an end-to-end anastomosis with eversion of the ends of the anatomical vessels 6.

Figure 2A:
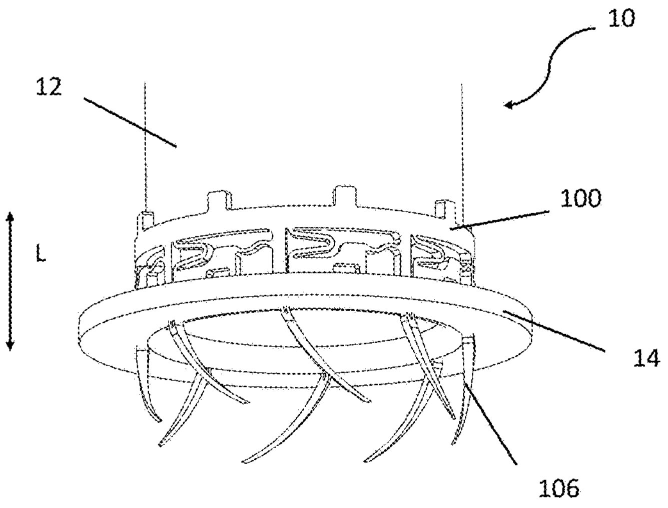
FIG. 2A is a perspective view of an exemplary sutureless mechanically active tine connector of the present disclosure coupled to a distal end of tubular graft.
Figure 2B:
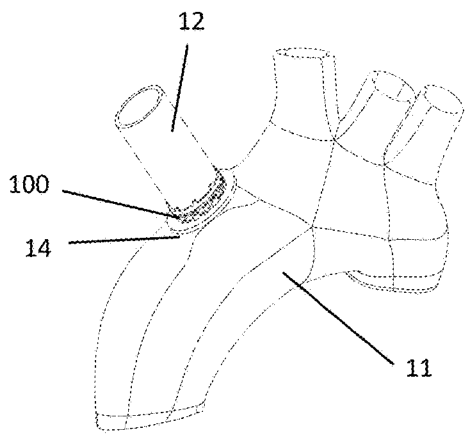
FIG. 2B is a perspective view of the sutureless mechanically active tine connector and tubular graft of FIG. 2A shown coupled to an aortic arch.
Figure 3:
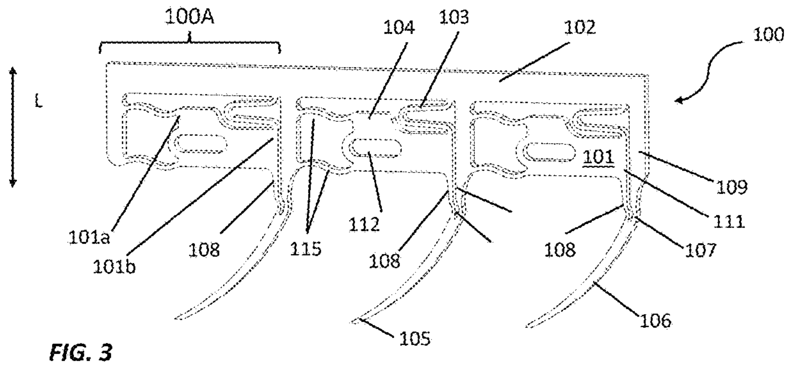
FIG. 3 is a side elevational view of a section of a first variant of the sutureless mechanically active tine connector in accordance with the present disclosure.

The connector 100, and its variants, is also capable of use as an end-to-side anastomosis connector as illustrated in FIG. 2A and FIG. 2B. An exemplary use of connector 100 is in forming an end-to-side anastomosis with the aorta 11. As is described in greater detail in co-pending U.S. patent application Ser. No. 18/458,398, filed Aug. 30, 2023, which is hereby incorporated by reference in its entirety, the connector 100 is coupled to a graft 12 and a plurality of mechanically active tines 106 extend into and through a hemostatic ring 14, such as a polytetrafluoroethylene felt ring. When brought into approximation with anatomical tissue, the mechanically active tines 106 penetrate into the anatomic tissue and draw the graft 12 and the connector 100 distally into connection with the anatomic tissue with the hemostatic ring 14 abutting the anatomic tissue and the mechanically active tines embedded into the anatomic tissue. As noted, the anatomic tissue may be, for example, a major blood vessel, e.g., the aorta 11, as illustrated in FIG. 2B. Alternatively, the anatomic tissue may be a peripheral blood vessel, skin, an anatomic passageway, or other anatomic tissue or non-anatomic tissue, such as another synthetic graft. In this manner, the graft 12 will serve as a conduit for fluid flow or access through a lumen of the graft 12 and into the anatomic or non-anatomic tissue to which it is attached via connector 100, or its variants described herein.

Thus, those skilled in the art will understand and appreciate that the connector 100 and its variants of the present disclosure are configured for making end-to-end and/or end-to-side connections, including, without limitations, end-to-end anastomosis and/or end-to-side anastomosis of anatomic tissues. Further, where an end-to-end anastomosis is desired, the anastomosis may be a butt-end anastomosis or an everted anastomosis in which one or both ends of the tissue being joined are everted to form a flange that is then joined together, such as is illustrated in FIGS. 1B and 1C.

The variants of connector 100 of the present disclosure generally include mechanically active tine rings, mechanically active serpentine tine rings, mechanically active tine staples, and/or mechanically active everting tine rings as depicted in the accompanying Figures and described herein. It is expressly intended and contemplated that the hereinafter described elements of each of the variants of connector 100 are to be considered interchangeable with one another and/or may be assembled in different configurations such that the functionality of each variant is preserved. For example, the configurations or geometries of the expansive members, the stabilizing members, the tension members, the compression members, the actuating members, may all be varied consistent with their intended operation and function as components of the hereinafter described tine assemblies and the connector variants.

Turning now to the specific variants of connector 100 illustrated in the accompanying Figures, a first connector variant 100 consists generally of a frame 102 that defines a ring or a linear or planar structure, an actuating member 104, and a tine 106. The tine 106 is operably coupled to the actuating member 104 by a first projection 108 extending from the actuating member 104. The tine 106 is also operably coupled to the frame 102 by a second projection 109 that extends from the frame. The tine 106 further has a hinge region 107 at a proximal end of the tine 106 that is coupled to both the first projection 108 and the second projection 109. The hinge region 107 is configured to act as a fulcrum to allow the tine 106 to traverse an arcuate path proximally and/or distally relative to the frame 102. An opening 111 separates the first projection 108 from the second projection 109 and terminates at or proximate to the hinge region 107 of the tine 106. Opening 111 is generally along a longitudinal axis L of the connector 100. Optionally, a strain relief opening 110 is provided in the hinge region 107 and at the distal end of the opening 111. Strain relief opening 110 is configured to distribute bending stress and strain forces at the hinge region 107 and tension and compression forces acting on the first projection 108 and the second projection 109 as the tine 106 moves proximally or distally relative to the frame 102.

Actuating member 104 is operably coupled to the frame and is configured to translate proximally and distally relative to the frame member 102 along longitudinal axis L. In connector 100, the actuating member 104 includes a main body 101, at least one stabilizing member 115, and at least one expansive member 103. The main body 101 may, optionally, have a recess or opening 112 configured to receive an engagement portion of a delivery device (not shown) that engages with the recess or opening 112 to translate the main body 101 proximally and/or distally relative to the frame 102.

The at least one stabilizing member 115 comprises a deformable member that projects laterally on one end thereof, from the second projection 109 extending from frame 102. At an opposite end of the deformable member of the at least one stabilizing member 115, the deformable member connects with the main body 101. Thus, the at least one stabilizing member 115 extends between the second projection 109 and the main body 101 on a first portion 101*a* of the main body 101. The at least one stabilizing member 115 may be linear, curvilinear, or have simple or complex curves along its length.

At a second portion 101*b* of the main body 101, the at least one expansive member 103 connects to the main body 101 and the frame 102. The first portion of the main body 101 and the second portion of the main body 101 are preferably located at opposite aspects of the main body 101. In this manner, translation of the main body 101 along a longitudinal axis of the connector 100, either proximally or distally relative to the frame 102, is stabilized by the at least one stabilizing member 115 and the expansive member 103. Further, in this manner, the main body exerts a linear force to the first projection 108 that is substantially parallel to the longitudinal axis of the connector 100. The linear force exerted by the first projection 108 acts at the hinge region 107 to deflect the tine 106. In this manner, either proximal or distal movement of the main body 101 deflects the tine 106 either proximally or distally, respectively.

The at least one expansive member 103 may have a myriad of configurations, provided that it is configured to expand and/or contract along the longitudinal axis of the connector 100. The at least one expansive member 103 may be a single generally V-shaped, U-shaped, hemi-elliptical, semi-circular, or similar shapes. Alternatively, the at least one expansive member 103 may be generally V-shaped, U-shaped, hemi-elliptical, semi-circular, or similar shapes, arranged in series or in parallel.

It is important to note that when the main body 101 is translated proximally relative to the frame 102, the first projection 108 is in a state of compression and the second projection 109 is in a state of tension, thereby allowing the tine 106 to rotate about the hinge region 107 in a proximal direction. Conversely, when the main body 101 is translated distally relative to the frame 102, the first projection 108 is in a state of tension and the second projection 109 is in a state of compression, thereby allowing the tine to rotate about the hinge region 107 in a distal direction. As the tine 106 rotates in a proximal direction, the tine 106 will compress anatomic tissue into which the tine 106 is embedded against the main body 101 and the frame 102. Whereas as the tine 106 rotates in a distal direction, the tine 106 will decompress the anatomic tissue into which the tine 106 is embedded and allow for release or removal of the connector 100 from the anatomic tissue. FIGS. 21-24 illustrate this functionality.

Connector 100, and each of its variants, may be made entirely or partially of an elastically or plastically deformable material, such as, for example, stainless steel, cobalt-chromium alloys, a shape memory or superelastic material, such as nickel-titanium based alloys, polymers, or combinations thereof, or may be made of bioresorbable polymeric materials.

Variants of connector 100 are depicted in FIGS. 4 to 19 and each embodies the same fundamental functional principals as connector 100 described above. That is, each variant has a frame, at least one actuating member, at least one stabilizing member, at least one expansive member, a first projection extending distally from the frame, a second projection extending distally from the at least one actuating member, and at least one tine projecting from both the first projection and the second projection, with the at least one tine having a hinge region. Moreover, in each of the variants of connector 100, there is provided a variant of the first projection 108 and the second projection 109 that act to carry compression and/or tension forces as the variant of the actuating member 104 is moved proximally and or distally relative to the variant of the frame 102.

Each of the variants of connector 100 may consist of either a single tine assembly 100A or plural tine assemblies 100A coupled to the frame. Each tine assembly of each variant includes at least one expansive member, an actuating member, optionally, at least one stabilizing member, a first projection extending distally from the frame, a second projection extending distally from the at least one actuating member, and at least one tine projecting from both the first projection and the second projection, with the at least one tine having a hinge region at its juncture with the first projection and/or the second projection.

Figure 4:
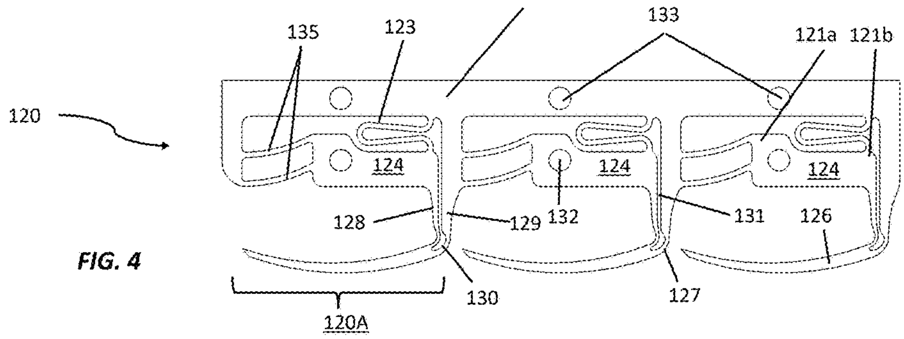
FIG. 4 is a side elevational view of a section of a second variant of the sutureless mechanically active tine connector in accordance with the present disclosure.

Turning to FIG. 4, a first connector variant 120 is illustrated. First connector variant 120 comprises a frame 122, which optionally, may have at least one of a plurality of openings 133 passing therethrough. Like connector 100, first connector variant 120 may include one or more tine assemblies 120A, with each tine assembly 120A including at least one expansive member 123, at least one actuating member 124, at least one stabilizing member 135 extending between the frame 122 and the at least one actuating member 124, an optional opening 132 passing through the at least one actuating member 124, at least one tine 126. The at least one tine 126 may be helically oriented in either a clockwise or counterclockwise direction relative to the longitudinal axis of the connector 120. The at least one time 126 is operably connected to both the frame 122 and to the at least one actuating member 124, and a hinge region 127 at a proximal aspect of the at least one tine 126. The at least one tine 126 is preferably tapered distally to a tapered end 125 that assists in penetrating into anatomic tissue. A first projection 128 extends distally from the at least one actuating member 124 and is connected to the hinge region 127 of the at least one tine 126. A second projection 129 extends distally from the frame 122 and is also connected to the hinge region 127 of the at least one tine 126. An opening 131 separates the first projection 128 and the second projection 129. Optionally, opening 131 terminates in a strain relief section 130 at the hinge region 127 of tine 126.

The at least one stabilizing member 135 comprises a deformable member that projects laterally on one end thereof, from the second projection 129 extending from frame 122. At an opposite end of the deformable member of the at least one stabilizing member 135, the at least one stabilizing member connects with a first portion 121*a* of the main body 121. Thus, the at least one stabilizing member 135 extends between the second projection 129 and the main body 121 and joins the first portion 121*a* of the main body 121. The at least one stabilizing member 135 may be linear, curvilinear, or have simple or complex curves along its length.

At a second portion 121*b* of the main body 101, the at least one expansive member 123 connects to the main body 121 and the frame 122. The first portion of the main body 121*a* and the second portion of the main body 121*b* are preferably located at opposite aspects of the main body 121. In this manner, translation of the main body 121 along a longitudinal axis of the connector 120, either proximally or distally relative to the frame 122, is stabilized by the at least one stabilizing member 135 and the expansive member 123. This arrangement stabilizes the main body 121 and allows the longitudinal translation of both the first portion 121*a* and the second portion 121*b* of the main body to move evenly along the longitudinal axis L. Further, in this manner, the main body exerts a linear force to the first projection 128 that is substantially parallel to the longitudinal axis of the connector 120. The linear force exerted by the first projection 128 acts at the hinge region 127 to deflect the tine 126. In this manner, either proximal or distal movement of the main body 121 deflects the tine 126 either proximally or distally, respectively.

As indicated above, the first projection 128 and the second projection 129 are configured to carry compression and/or tension forces as the at least one actuating member 124 is moved proximally and or distally relative to the frame 122 and rotates the at least one tine 126 either proximally or distally about the hinge region 127.

Frame 122 may also be configured as a ring or a linear or planar structure and be provided with plural first projections 128, second projections 129, actuating members 124, and tines 126.

Figure 5:
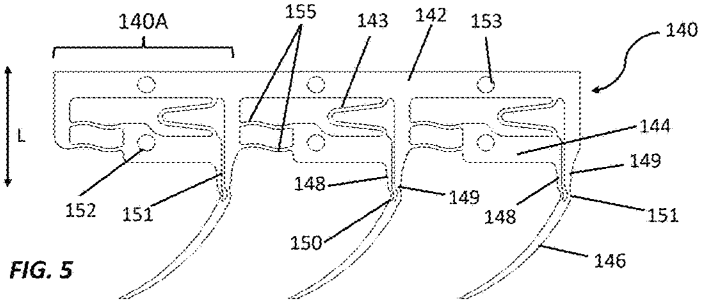
FIG. 5 is a side elevational view of a section of a third variant of the sutureless mechanically active tine connector in accordance with the present disclosure.

FIG. 5 illustrates a second variant of connector 140 of the present disclosure. Connector 140 is virtually identical to connector 120 of FIG. 4, with the exception that the at least one stabilizing member 155 has a sinusoidal shape as opposed to the curvilinear shape of the at least one stabilizing member 135 of connector 120. Otherwise, the connector 140 includes the same functionality and structural elements as connector 120 and consists of one or more tine assemblies 140A including a frame 142 defining a ring or a linear or planar structure, an actuating member 144, and at least one tine 146. The at least one tine 146 may be helically oriented in either a clockwise or counterclockwise direction relative to the longitudinal axis of the connector 140. The at least one tine 146 is operably coupled to the actuating member 144 by a first projection 148 extending from the actuating member 144. The at least one tine 146 is also operably coupled to the frame 142 by a second projection 149 that extends from the frame. The tine 146 further has a hinge region 147 at a proximal end of the tine 146 that is coupled to both the first projection 148 and the second projection 149. The hinge region 147 is configured to act as a fulcrum to allow the tine 146 to traverse an arcuate path proximally and/or distally relative to the frame 142. An opening 151 separates the first projection 148 from the second projection 149 and terminates at or proximate to the hinge region 147 of the tine 146. Optionally, a strain relief opening 150 is provided in the hinge region 147 and at the distal end of the opening 151. Strain relief opening 150 is configured to distribute bending stress and strain forces at the hinge region 147 and tension and compression forces acting on the first projection 148 and the second projection 149 as the tine 146 moves proximally or distally relative to the frame 142.

Figure 6:
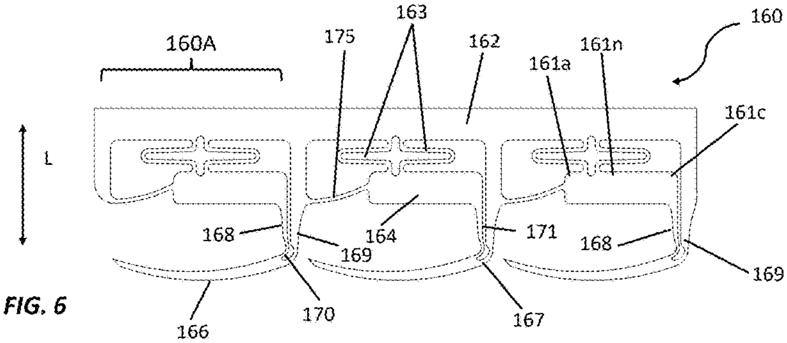
FIG. 6 is a side elevational view of a section of a fourth variant of the sutureless mechanically active tine connector in accordance with the present disclosure.

Turning to FIG. 6, a third connector variant 160 is illustrated. Second connector variant 160 is similar to connector 100, except that at least two expansive members 163 are provided and arranged in parallel. The at least two expansive members 163 have their vertices oriented in opposite directions relative to the frame 162 and also expand along a longitudinal axis of the frame 162. The at least two expansive members 163 are each joined with the frame 162 on first end thereof and to an actuating member 164 at a second end thereof. The juncture 161*c* of the at least two expansive members 163 with the frame 162 is positioned at a point between the first portion 161*a* and the second portion 161*b* of the actuating member 164. As with other variants of connector 100, at least one stabilizing member 175 is provided that extends laterally from a second projection 169 from frame 162 and joins with the actuating member 164 at or proximate to the first portion 161*a* of the at least one actuating member 164.

An optional opening may be provided that passes through the at least one actuating member 164. The at least one tine 166 operably connected to both the frame 162 and to the at least one actuating member 164. The at least one tine 166 may be helically oriented in either a clockwise or counterclockwise direction relative to the longitudinal axis of the connector 160. The at least one tine 166 has a hinge region 167 at a proximal aspect of the at least one tine 166. The at least one tine 166 is preferably tapered distally to a tapered end 165 that assists in penetrating into anatomic tissue. The first projection 168 extends distally from the at least one actuating member 164 and is connected to the hinge region 167 of the at least one tine 166. A second projection 169 extends distally from the frame 162 and is also connected to the hinge region 167 of the at least one tine 166. An opening 171 separates the first projection 168 and the second projection 169 along longitudinal axis L. Optionally, opening 171 terminates in a strain relief section 170 at the hinge region 167 of tine 166.

The at least one stabilizing member 175 comprises a deformable member that projects laterally on one end thereof, from the second projection 169 extending from frame 162. At an opposite end of the deformable member of the at least one stabilizing member 175, the at least one stabilizing member 175 connects with a first portion 161*a* of the actuating member 164. Thus, the at least one stabilizing member 175 extends between the second projection 169 and the actuating member 164 and joins to the first portion 161*a* of the actuating member 164.

It will be appreciated by those skilled in the art that longitudinal translation of the main body 164 along a longitudinal axis L of the connector 160, either proximally or distally relative to the frame 162, is stabilized by the at least one stabilizing member 175 and the at least two expansive members 163. Further, in this manner, the actuating member 164 exerts a linear force to the first projection 168 that is substantially parallel to the longitudinal axis L of the connector 160. The linear force exerted by the first projection 168 acts at the hinge region 167 to deflect the tine 166. In this manner, either proximal or distal movement of the actuating member 164 deflects the tine 166 either proximally or distally, respectively, relative to the frame 162.

As indicated above, the first projection 168 and the second projection 169 are configured to carry compression and/or tension forces as the at least one actuating member 164 is moved proximally and or distally relative to the frame 162 and rotates the at least one tine 166 either proximally or distally about the hinge region 167.

Frame 162 may also be configured as a ring or a linear or planar structure and be provided with one or plural tine assemblies 160A including plural first projections 168, second projections 169, actuating member(s) 164, and tines 166.

Figure 7:
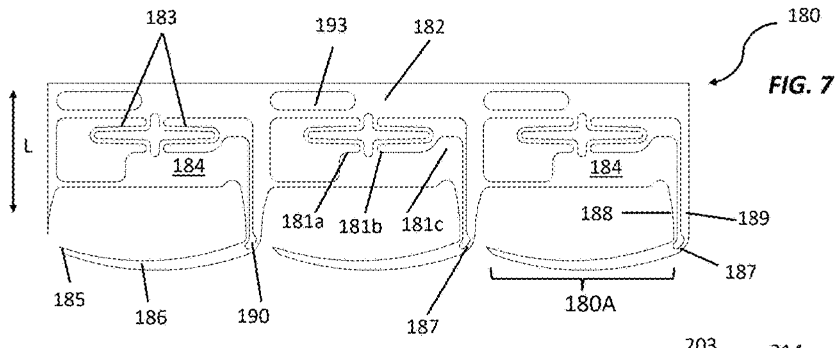
FIG. 7 is a side elevational view of a section of a fifth variant of the sutureless mechanically active tine connector in accordance with the present disclosure.

A fourth variant connector 180 is depicted in FIG. 7. Connector 180 is virtually identical to connector 160, with the exception that at least one opening 193 is provided and passes through the frame 182 and the at least one stabilizing member 195 joins the actuating member 184 at a different position and is substantially linear rather than the curved configuration of the at least one stabilizing member 175. The at least one opening 193 is provided and may serve as a coupling point for a delivery device and/or may service as an opening for an adhesive to join the frame 182 to a graft (not shown). Otherwise, connector 180 is substantially the same as connector 160 in that it includes at least two expansive members 183 arranged in parallel. The at least two expansive members 183 have their vertices oriented in opposite directions relative to the frame 182 and also expand along a longitudinal axis of the frame 182. The at least two expansive members 183 are each joined with the frame 182 on first end thereof and to an actuating member 184 at a second end thereof. The juncture 181*c* of the at least two expansive members 183 with the frame 182 is positioned at a point between the first portion 181*a* and the second portion 181*b* of the actuating member 184. As with other variants of connector 100, at least one stabilizing member 195 is provided that extends laterally from a second projection 189 from frame 182 and joins with the actuating member 184 at or proximate to the first portion 181*a* of the at least one actuating member 184.

Frame 182 may also be configured as a ring or a linear or planar structure and be provided with one or plural tine assemblies 180A including plural first projections 188, second projections 189, actuating member(s) 184, and tines 186. Tines 186 may be helically oriented in either a clockwise or counterclockwise direction relative to the longitudinal axis of the connector 180.

Figure 8:
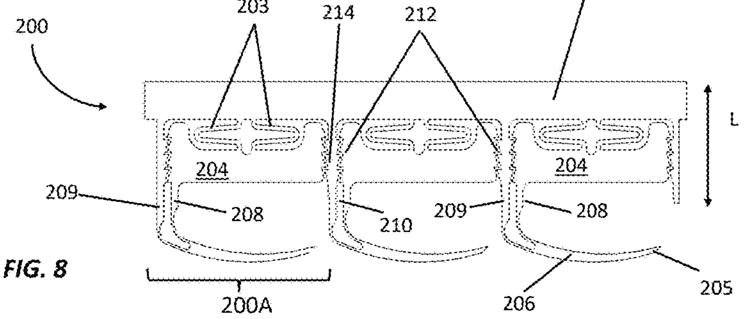
FIG. 8 is a side elevational view of a section of a sixth variant of the sutureless mechanically active tine connector in accordance with the present disclosure.

Fifth variant connector 200 is shown in FIG. 8. Like connector 180, connector 200 employs at least two expansive members 203. The at least two expansive members 203 are provided and arranged in parallel. The at least two expansive members 203 have their vertices oriented in opposite directions relative to the frame 202 and also expand along a longitudinal axis of the frame 202. The at least two expansive members 203 are each joined with the frame 202 at substantially a mid-point of a proximal aspect of an actuating member 204. By positioning the junction between the at least two expansive members 203 at a substantial mid-point of the actuating member 204, the actuating member 204 will translate substantially along a longitudinal axis without the need for a stabilizing member, such as stabilizing member 195. Further, like connector 180, connector 200 has a first projection 208 that extends from the actuating member 204 and a second projection 209 that extends from the frame 202. Also, connector 200 has a tine 206 joined to each of the first projection 208 and the second projection 209 at a proximal aspect of the tine 206. An opening 211 extends between the first projection 208 and the second projection 209. An optional strain relief opening 210 may be positioned at a hinge region 207 at the juncture between the proximal aspect of the tine 206 and its juncture with the first projection 208 and the second projection 209. Tine 206 may be helically oriented in either a clockwise or counterclockwise direction relative to the longitudinal axis of the connector 200.

Distinct from the previously described connector variants, connector 200 employs a plurality of first engagements 212 on each lateral edge of the actuating member 204 and a plurality of engagements 214 on each lateral surface of the second projections extending from the frame 202. The plurality of first engagements 212 and the plurality of second engagements 214 are configured to mate with each other, allow the actuating member 204 to translate along the longitudinal axis of the frame 202, and maintain alignment of each lateral surface of the actuating member 204 as it translates within the frame 202 in a linear manner. The plurality of engagements 212 and the plurality of engagements 214 may be any of a wide variety of engaging interfaces, for example, mating projections and detents, rachet, track and follower, or other similarly functional linear motion engagements.

Frame 202 may also be configured as a ring or a linear or planar structure and be provided with one or plural tine assemblies 200A including plural first projections 208, second projections 209, actuating member(s) 204, tines 206, first engagements 212, and second engagements 214.

Figure 9:
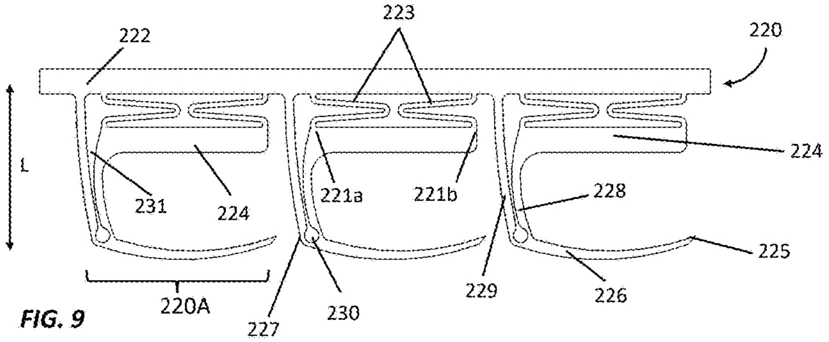
FIG. 9 is a side elevational view of a section of a seventh variant of the sutureless mechanically active tine connector in accordance with the present disclosure.

Sixth connector variant 220 is shown in FIG. 9. Like connector 180, connector 220 employs at least two expansive members 223 arranged in parallel to each other. The at least two expansive members 223 may be generally V-shaped, U-shaped, hemi-elliptical, semi-circular, or similar shapes. The at least two expansive members 223 have their vertices oriented toward each other relative to the frame 222 and are capable of expansion and contraction along longitudinal axis L. The at least two expansive members 223 also expand along a longitudinal axis of the frame 222. The at least two expansive members 223 are each joined with the frame 222 at substantially a mid-point of a proximal aspect of an actuating member 224. A junction between the at least two expansive members 223 is at a substantial mid-point of the actuating member 224. In this manner the actuating member 224 will translate substantially along longitudinal axis L without the need for a stabilizing member, such as stabilizing member 195. Further, like connector 180, connector 220 has a first projection 228 that extends from the actuating member 224 and a second projection 229 that extends from the frame 222. Also, connector 220 has a tine 226 joined to each of the first projection 228 and the second projection 229 at a proximal aspect of the tine 226. Tine 226 may be helically oriented in either a clockwise or counterclockwise direction relative to the longitudinal axis of the connector 220. An opening 231 extends between the first projection 228 and the second projection 229. Opening 231 isolates the tension and compression forces applied to the first projection 228 and the second projection 229. An optional strain relief opening 230 may be positioned at a hinge region 227 at the juncture between the proximal aspect of the tine 226 and its juncture with the first projection 228 and the second projection 229. Tine 226 may, optionally, be tapered to a distal point 225 to facilitate penetration of the tine 226 into anatomical tissue.

As with other variants, the first projection 228 and the second projection 229 are configured to act to carry either compression or tension forces depending upon whether the actuating member 224 and the expansive members 223 are being expanded or contracted relative to the longitudinal axis L of connector 220.

Like other variants of the connector 100, the frame 222 of connector 220 may be formed as a planar or linear member or as a ring member. A tine assembly 220A includes the at least two expansive members 223, the first projection 229, the second projection 228, tine 226, and, optionally, strain relief section 230. Plural tine assemblies 220A may be arrayed in series along the frame 222 with the plurality of tines 226 being having a common orientation relative to the frame 222 or having alternating orientations relative to the frame 222.

Figure 10:
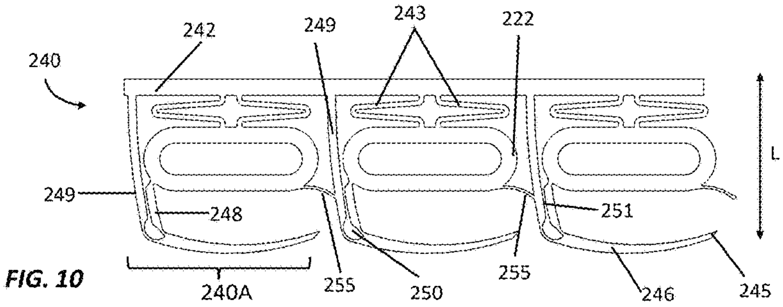
FIG. 10 is a side elevational view of a section of an eighth second variant of the sutureless mechanically active tine connector in accordance with the present disclosure.

A seventh connector variant 240 is shown in FIG. 10. Connector 240 is similar to connector 180 with the major difference being that the actuation member 244 is configured of an open ring structure. The open ring actuation member 244 reduces the mass of the actuation member 244 as compared with another structure or geometry of the actuation member and may, optionally, serve as a coupling for a delivery device. Otherwise, like connector 180, connector 240 may include one or more tine assemblies 240A, each tine assembly 240A including the at least two expansive members 243, the first projection 249, the second projection 248, tine 246, and, optionally, strain relief section 250. Plural tine assemblies 240A may be arrayed in series along the frame 242 with the plurality of tines 246 being having a common orientation relative to the frame 242 or having alternating orientations relative to the frame 242. Tine 246 or the plurality of tines 246 may be helically oriented in either a clockwise or counterclockwise direction relative to the longitudinal axis of the connector 240.

The at least two expansive members 243 may be generally V-shaped, U-shaped, hemi-elliptical, semi-circular, or similar shapes. The at least two expansive members 243 have their vertices oriented away from each other relative to the frame 242 and are capable of expansion and contraction along longitudinal axis L. The at least two expansive members 243 are each joined with the frame 242 on first end thereof and to an actuating member 244 at a second end thereof. The juncture of the at least two expansive members 243 with the frame 242 is positioned at a point intermediate along a length of the actuating member 244. At least one stabilizing member 255 is provided that extends laterally from a second projection 249 from frame 242 and joins with the actuating member 242. An elongate opening 251 separates the first projection 248 from the second projection 248 and isolates compression and tension forces applied to the first projection 248 and the second projection 248. The elongate opening 251 terminates in an optional strain relief opening 250 at a hinge region 247 at a junction between the tine 246 and the first projection 248 and second projection 249. As with other variants, each of the at least one tine 246 may, optionally, have a distal taper that terminates in a tapered point 245 to facilitate penetration of the at least one tine 246 into anatomic tissue.

Turning now to other variants of the connector 100 in which there are no expansive members employed that are configured to act upon an actuating member. Rather, in the following variants, the actuating member is joined to a first projection and a second projection only or additionally to plural stabilizing members. In each of the following variants of connector 100, there may also be provided one or more tine assemblies arrayed along a common frame member.

Figure 11:
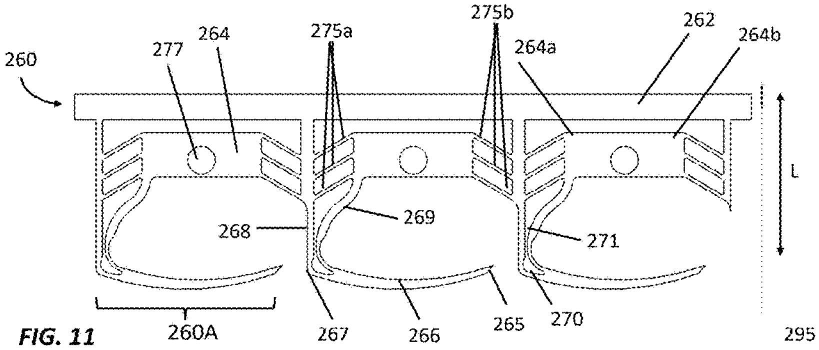
FIG. 11 is a side elevational view of a section of a ninth variant of the sutureless mechanically active tine connector in accordance with the present disclosure.

According to an eighth connector variant 260 in FIG. 11, there is provided a connector 260. Connector 260 foregoes employing expansive members and like other variants has a frame 262, an actuating member 264, a first projection 268 extending longitudinally from the frame 262 and a second projection 269 extending from the actuating member 264. At least one tine 266 is joined to both the first projection 268 and the second projection 269 at a hinge region 267 between a proximal aspect of the tine 266 and distal aspects of each of the first projection 268 and second projection 269. An elongate opening 271 separates the first projection 268 from the second projection and terminates in an optional strain relief opening 270 at the hinge region 267. Plural stabilizing members 275 project from opposite ends of the actuating member 264, with a first set of stabilizing members **275*a* projecting from a first end 264*a* of the actuating member 264 and a second set of stabilizing members 275*b* projecting from a second end 264*b* of the actuating member 264. Both the first set of stabilizing members 275*a* and the second set of stabilizing members 275*b* join with a respective first projection 268 from the frame 262. Optionally, an opening 277 is provided that passes through the actuating member 264 that is configured to serve as a coupling point for a delivery device to facilitate translation of the actuating member 264 relative to frame 262. The at least one tine 266 may be helically oriented in either a clockwise or counterclockwise direction relative to the longitudinal axis of the connector 260**.

Connector 260 may include one or more tine assemblies 260A, each tine assembly 260A including the first projection 269 and the second projection 268 isolated from each other by opening 271, tine 266, stabilizing members **264*a* and 264*b*, actuating member 264, and, optionally, strain relief section 250. Plural tine assemblies 260A may be arrayed in series along the frame 262 with the plurality of tines 266 having a common orientation relative to the frame 262 or having alternating orientations relative to the frame 262**.

It will be understood by those skilled in the art that translation of the actuating member 264 along the longitudinal axis L of the connector 260 will cause the plural stabilizing members 275 to deform synchronously, thereby exerting concomitant tension and compression forces onto the first projection 268 and second projection 269 and provide a motive force to cause rotation of the tine 266 about hinge region 267. In this manner, the at least one tine 266 will rotate about hinge region 267 to either an open or closed position to allow either the delivery and penetration into anatomic tissue or compression of anatomic tissue between the at least one tine 266 and the actuating member 264, respectively.

Figure 12:
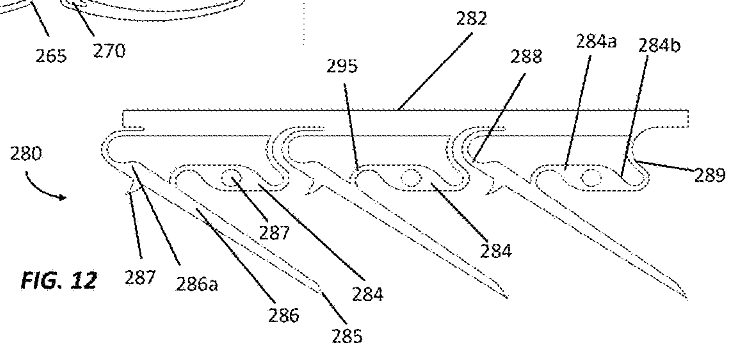
FIG. 12 is a side elevational view of a section of a tenth variant of the sutureless mechanically active tine connector in accordance with the present disclosure.

A ninth connector variant 280 is illustrated in FIG. 12. According to this ninth connector variant 280, the actuating member 284 is carried on frame 282 by a tine 286 joined to a first projection 288 on a first end **284*a* of the actuating member 284 and at a second end 284*b* of the actuating member 284 to a second projection 289 extending from frame 282. A proximal portion of the first projection 288 extends from frame 282 and curves, in a generally hemi-elliptical shape, to join to a proximal end 286*a* of an associated tine 286. The first end 284*a* of actuating member 284 is joined by an actuating projection 295 to an associated tine 286 distally from the junction of the first projection 288** with the tine 286. The second end 284*b* of the actuating member 284 is joined to the frame 282 by the second projection 289. Second projection 289 projects from frame 282 in a generally curved manner, such as a generally serpentine shape, and joins with the second end 284*b* of the actuating member 284. In this manner, the actuating member 284 joins with both the tine 286 and the frame 282 such that longitudinal translation of the actuating member 284 along the longitudinal axis of connector 280 imparts compression and/or tension forces on the first projection 288 and the second projection 289 and moves the tine 286 in a rotational manner about the first projection 288 due to its curvilinear shape. In this manner, the first projection 288 operates and is configured to function as a hinge about which the tine 286 rotates. Each tine 286 may be helically oriented in either a clockwise or counterclockwise direction relative to the longitudinal axis of the connector 280.

Optionally, an opening 287 passes through the actuating member 284 and is configured to engage with a delivery device (not shown) to allow for longitudinal translation of the actuating member 284 and delivery of the connector 280 into anatomic tissue.

Finally, in contrast to other variants of the connector 100, connector 280 employs linear tines 286, as opposed to curved tines, such as those illustrated in connector 260. To assist in embedding and retention of the tines 286 in the anatomic tissue, where linear tines 286 are employed, it is advantageous, but optional, to provide a barb 287 at a proximal region of the tine 286.

Figure 13:
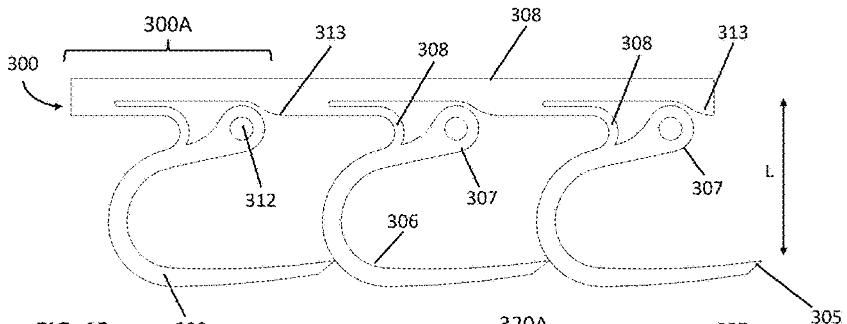
FIG. 13 is a side elevational view of a section of an eleventh variant of the sutureless mechanically active tine connector in accordance with the present disclosure.

Another connector variant 300 is illustrated in FIG. 13. Connector 300 employs a somewhat different rotational operation of the tines than other variants described herein. Like other connector variants described herein, connector 300 includes a frame 302 that carries at least one of a plurality of connector assemblies 300A. Each of the at least one of a plurality of tine assemblies 300A consists of a generally C-shaped tine 306 that is joined at its proximal end to a first projection 308. Each generally C-shaped tine may be oriented in either a clockwise or counterclockwise direction relative to the longitudinal axis of the connector 300. First projection 308 extends from frame 302 and is curvilinear. A pivot section 307 is also joined at the proximal end of the generally C-shaped tine 306. Pivot section 307 consists of a rounded portion having an opening 312. Opening 312 is configured to engage with a delivery device (not shown) that that is configured to translate the pivot section 307 and rotate the tine 306 about the first projection 308. In this manner the first projection 308 acts as a hinge to allow the tine 306 to rotate in a plane both proximally and distally about the first projection 308 and allow the distal end 305 of tine 306 to engage anatomic tissue and compress the anatomic tissue between frame 302 and tine 306. The frame 302 may, optionally, have an abutment portion 313 that is configured to allow the pivot section 307 to abut against frame 302 when the pivot section 307 of tine 306 is in a deployed state with the tine 306 embedded into anatomic tissue. In contrast, when the tine 306 is in a delivery state, the pivot section 308 or tine 306 will be rotated distally away from frame 302.

Connector 300 may include one or more tine assemblies 300A, each tine assembly with plural tine assemblies 300A may be arrayed in series along the frame 302 with the plurality of tines 306 having a common orientation relative to the frame 302 or having alternating orientations relative to the frame 302.

Figure 14:
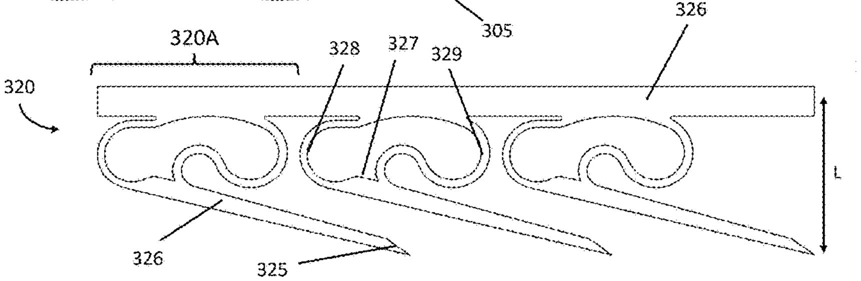
FIG. 14 is a side elevational view of a section of a twelfth variant of the sutureless mechanically active tine connector in accordance with the present disclosure.

FIG. 14 illustrates an eleventh connector variant 320. Unlike other variants, connector 320 does not employ an actuating member. Thus, connector 320 is well suited to be made of shape memory or superelastic materials. In connector variant 320, a frame 322 carries at least one tine assembly 320A, with each tine assembly 320A consisting of a linear tine 326 joined at its proximal end 327 to a first projection 328 and a second projection 329. Each of the first projection 328 and the second projection 329 are also joined to the frame 322 and have a generally curvilinear shape, with the first projection 328 having a generally semi-circular profile and the second projection 329 having a generally serpentine profile. The first projection 328 is configured to projects axially from the proximal end 327 of tine 326, while the second projection 329 is joined to a lateral surface of the proximal end 327 of tine 326 and positioned distally from the junction of the first projection 328 with tine 326. In this manner, the junctions of the first projection 328 and the second projection 329 with the tine 326 acts as a lever to allow the tine 326 to rotate about the junctions in a hinge-like manner. Each linear 326 may be helically oriented in either a clockwise or counterclockwise direction relative to the longitudinal axis of the connector 320.

As with other variants, the tine 326 has a distal taper and terminates in a distal tip 325 that is configured to permit the tine to penetrate and embed in anatomic tissue. While not shown in FIG. 14, an optional barb may project from a lateral surface of tine 326 proximate to proximal end 326 of the tine 326 to further assist in embedding the tine 326 in the anatomic tissue.

Connector 320 may include one or more tine assemblies 320A, each tine assembly with plural tine assemblies 320A may be arrayed in series along the frame 322 with the plurality of tines 326 having a common orientation relative to the frame 322 or having alternating orientations relative to the frame 322.

Figure 15:
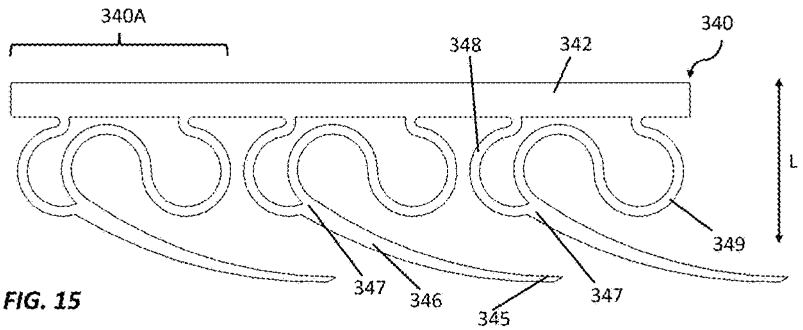
FIG. 15 is a side elevational view of a section of a thirteenth variant of the sutureless mechanically active tine connector in accordance with the present disclosure.

FIG. 15 illustrates a twelfth variant connector 340. Connector 340 is similar to connector 320 in that it has a frame 342, a first projection 348 from frame 342, a second projection 349 from frame 342, with both the first projection 348 and the second projection being joined at a second end to a proximal end 347 tine 346. Each tine 346 may be helically oriented in either a clockwise or counterclockwise direction relative to the longitudinal axis of the connector 340. The first projection 348 has a generally C-shaped curvature while the second projection 349 has a generally S-shaped curvature, with both the first projection 348 and the second projection 349 joining at the proximal end 347 of tine 346. Tine 346 has a curvilinear profile that curves proximally, i.e., toward the frame 362, and tapers to a distal tip 345.

Connector 340 may include one or more tine assemblies 340A, each tine assembly with plural tine assemblies 340A may be arrayed in series along the frame 342 with the plurality of tines 346 having a common orientation relative to the frame 342 or having alternating orientations relative to the frame 342. Like connector 320, connector 340 does not employ an actuation member and is, therefore, well suited for use with shape memory or superelastic materials to actuate the tine 346.

Figure 16:
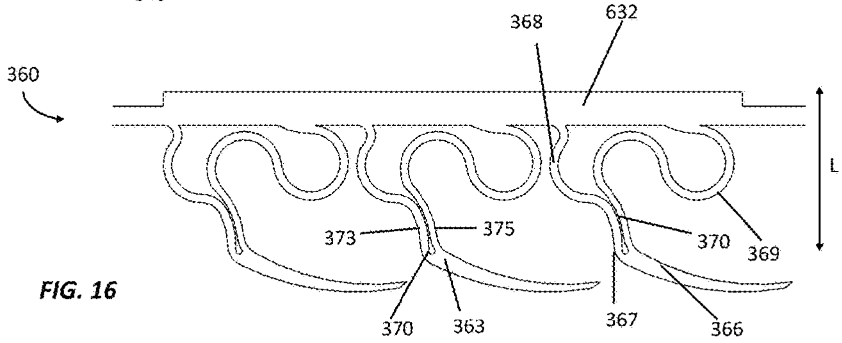
FIG. 16 is a side elevational view of a section of a fourteenth variant of the sutureless mechanically active tine connector in accordance with the present disclosure.

A thirteenth variant connector 360, which is similar to connector 340, is depicted in FIG. 16. Like connector 340, connector 360 does not employ an actuation member. Connector 360 may include one or more tine assemblies 360A, each tine assembly with plural tine assemblies 360A may be arrayed in series along the frame 362 with the plurality of tines 366 having a common orientation or having alternating orientations relative to the frame 362. Connector 360 includes a frame 362, a first projection 368 extending from the frame 362, a second projection 369 extending from the frame 362, and a curvilinear tine 366 that curves proximally, i.e., toward the frame 362, and tapers to a distal tip 365. The first projection 368 has a generally C-shaped profile with an elongated leg 373 that extends distally and joins with a hinge region 367 at a proximal end 363 of the tine 366. The second projection 369 has a generally S-shaped serpentine profile and also has an elongated leg 375 that extends distally and joins with the proximal end 363 of tine 366 at the hinge region 367. An elongate opening 371 separates the elongated leg 375 of the second projection 369 from the elongated leg 373 of the first projection 368. Optionally, a strain relief section 370 may be provided at the hinge region 367 to distribute stress and strain forces as the tine rotates about the hinge region 367.

Figure 17:
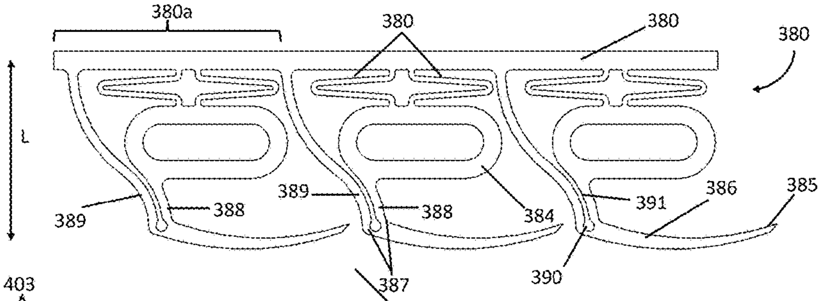
FIG. 17 is a side elevational view of a section of a fifteenth variant of the sutureless mechanically active tine connector in accordance with the present disclosure.

FIG. 17 illustrates a fourteenth variant connector 380. Connector 380 is similar to connector 240 in that it has a frame 382 and at least one mechanically active tine assembly 380A. Each of the at least one mechanically active tine assemblies 380A consist of an actuation member 384 that is configured as an open ring structure, at least two expansive members 383, a first projection 388 that extends distally from the actuation member 384, a second projection 389 that extends distally from the frame 382, and a tine 386 joined to distal ends of both the first projection 388 and the second projection 389. Each tine 386 may have a helically orientation in either a clockwise or counterclockwise direction relative to the longitudinal axis of the connector 120. The open ring actuation member 384 reduces the mass of the actuation member 384 as compared with a solid structure of the actuation member and may, optionally, serve as a coupling for a delivery device. Otherwise, like connector 240, connector 380 includes at least two expansive members 383 arranged in parallel such that they are configured to longitudinally expand and contract substantially simultaneously as the open ring actuation member is longitudinally translated relative to the frame 382. The at least two expansive members 383 are generally V- or U-shaped and have their respective vertices oriented in opposite directions relative to the frame 382 and also expand along a longitudinal axis of the frame 382. Other configurations of the at least two expansive members 383 are expressly contemplated as well, including, for example, serpentine shapes, provided that the expansive members 383 are capable of substantially simultaneous expansion and contraction in the longitudinal axis of the connector 380.

Connector 380 may include one or more tine assemblies 380A, each tine assembly with plural tine assemblies 380A may be arrayed in series along the frame 382 with the plurality of tines 386 having a common orientation or having alternating orientations relative to the frame 382.

The at least two expansive members 383 are each joined with the frame 382 at first ends thereof and, at second ends thereof to the actuating member 384. The juncture of the at least two expansive members 383 with the frame 382 is positioned at a point intermediate along a length of the actuating member 384. An elongate opening 391 separates the first projection 388 from the second projection 389 and terminates in an optional strain relief opening 390 at a hinge region 387 at a junction between the tine 386 and the first projection 383 and second projection 389. The first projection 388

As with other variants, each of the at least one tine 246 may, optionally, have a distal taper that terminates in a tapered point 245 to facilitate penetration of the at least one tine 246 into anatomic tissue. Unlike connector 240, no stabilizing member is provided to connect the actuation member 384 with the that extends laterally from a second projection 389 from frame 382.

The second projection 389 has a curvilinear configuration such that the proximal end and the distal end of the second projection 389 are offset from each other along the longitudinal axis of the connector 380.

Figure 18:
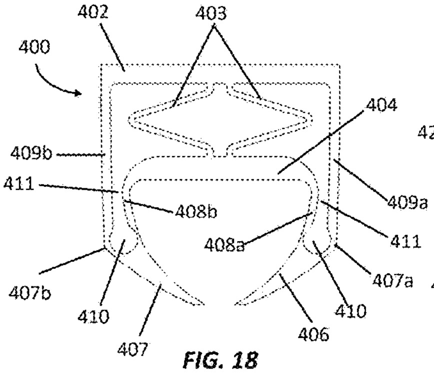
FIG. 18 is a first variant of a mechanically active tine staple connector in accordance with the present disclosure.
Figure 19:
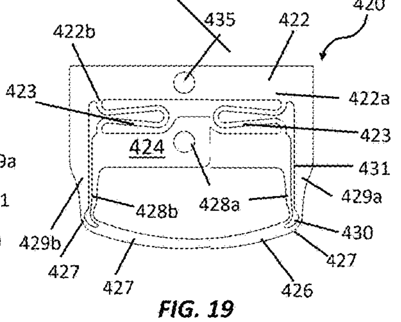
FIG. 19 is a side elevational view of second variant of a mechanically active tine staple connector in accordance with the present disclosure.
Figure 20:
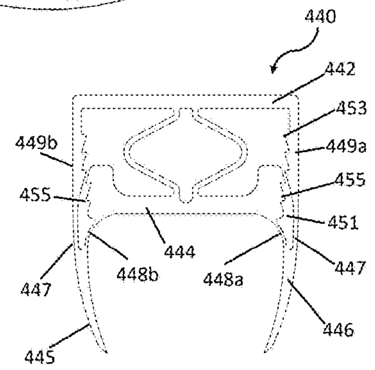
FIG. 20 is a side elevational view of a third variant of a mechanically active tine staple connector in accordance with the present disclosure.

Turning now to FIGS. 18 to 20 there is illustrated variants of staple-like mechanically active tine connectors 400, 420, and 440, respectively. Functionally, the staple-like mechanically active tine connectors 400, 420, and 440 operate similarly to the foregoing described variants of connector 100, with the major exception being that the mechanically active tine connectors 400, 420, and 440 employ dual opposing tines that deflect centrally inward and toward each other.

FIG. 18 illustrates a first variant of the staple-like connector 400 in which a frame 402 has a first frame projection **409*a* and a second frame projection 409*b* extending distally from the frame 402. At least one expansive member 403 is joined to the frame 402 on one end thereof and to an actuating member 404 on a second end. The actuating member 404 has at least a first actuating projection 408*a* and a second actuating projection 408*b* that extend distally from the actuating member 404. The first frame projection 409*a* and the first actuating projection 408*a* join to a proximal end of a first tine 407 at hinge region 407*a*, while the second frame projection 409*b* and the second actuating projection 408*b* join with a proximal end of a second tine 406 at hinge region 407*b*. Hinge regions 407*a*, 407*b*, serve as fulcrum points to allow the first and second tines 407, 406 to rotate proximally and/or distally under the influence of tension and/or compression forces exerted by translational movement of the actuating member 404 and the at least one expansive member 403. An optional strain relief opening 410 may be provided at the hinge regions 407*a*, 407*b* to distribute stress and strain forces at the hinge regions 407*a*, 407*b*. An opening 411 separates the first and second frame projections 409*a*, 409*b* from the first and second actuating projections 408*a*, 408*b* and allows for independent transfer of tension and/or compression forces from either the frame 402 and/or the actuating member 404 to the hinge regions 407*a*, 407*b* to actuate movement of the first and second tines 407, 406**.

FIG. 19 illustrates a second variant of the staple-like connector 420. Staple-like connector 420 also consists of a frame 422 having a first frame projection **429*a* and a second frame projection 429*b* extending distally from frame 422. At least two expansive members 423 are joined to the frame 422 at a first lateral portion 422*a* and a second lateral portion 422*b* of frame 422 at a first end of each of the at least two expansive members 423. The least two expansive members 423 are connected to an actuating member 424 at second ends thereof. In staple-like connector 420, the at least two expansive members 423 are configured as longitudinally expansive U-shaped or V-shaped members. It is contemplated, however, that the at least two expansive members 423 may have any shape provided that they are capable of expanding along the longitudinal axis of the staple-like connector 420 as the actuating member 424 is translated along the longitudinal axis of the staple-like connector 420. A frame opening 435 may, optionally, be provided in frame 422, and an actuating opening 433 may, optionally, be provided in actuating member 424. Frame opening 435 and actuating opening 433, when provided, may be configured to engage a delivery device (not shown) that actuates translational movement of the actuating member 424 relative to frame 422**.

An elongate opening 431 that, optionally, terminates in a strain relief opening 430, separates the first and second frame projections 429*a*, 429*b* from the first and second actuating projections 428*a*, 428*b*. In this manner, longitudinal translation of the actuating member 433 will exert tension and/or compression forces in the first and second frame projections 429*a*, 429*b* from the first and second actuating projections 428*a*, 428*b* and provide a motive force to first and second tines 425, 426 to rotate the first and second tines 425, 426 about hinge region 426, with distal ends of each of the first and second tines 425, 426 being brought into an approximating relationship when the staple-like connector 420 is in its closed position as depicted in FIG. 19.

FIG. 20 illustrates another variant of staple-like connector 440. Staple-like connector 440 also includes a frame 442 having a first frame projection 449*a* and a second frame projection 449*b* extending distally from the frame 442 and joined to a proximal end of a tine 445, 447, respectively, at a distal end of each of the first frame projection 449*a* and the second frame projection 449*b*. Expansive members 443 are joined at one end thereof to the frame 442 and at their other end to an actuating member 444. The expansive members 443 are configured as longitudinally expansive U-shaped or V-shaped members. It is contemplated, however, that the expansive members 433 may have any shape provided that they are capable of expanding along the longitudinal axis of the staple-like connector 440 as the actuating member 444 is translated along the longitudinal axis of the staple-like connector 440.

At least one of a plurality of engagements 453 are provided on an inner surface of each of the first frame projection 449*a* and the second frame projection 449*b*, i.e., that surface facing toward the actuating member 444. The at least one of a plurality of engagements 453 engage with a corresponding cooperating engagement 455 provided on lateral surfaces of the actuating member 444, i.e., the surfaces of the actuating member 444 facing the first frame projection 449*a* and the second frame projection 449*b*. The cooperating engagement between the at least one of a plurality of engagements 453 and the engagement 455 on the actuating member 444 is configured to allow for a substantially linear translation of the actuating member along the longitudinal axis of the connector 440. The engagement will also permit bidirectional adjustability of the positions of tines 445, 446 into a fixed position relative to frame 442 by the relative position of the actuating member relative to the frame 442.

With the exception of the cooperating engagement interface between the at least one of a plurality of engagements 453 and the engagement 455 on the actuating member 444, an opening 451 is provided between the first and second frame projections 449*a*, 449*b*, and a first actuating projection 448*a* and a second actuating projection 448*b*, respectively. Opening 51 permits the first and second frame projections 449*a*, 449*b*, to operate in tension and/or compression modes substantially independently of the first and second actuating projections 448*a*, 448*b* to transfer force to the respective tines 445, 447 and allow then to rotate about hinge region 447 at a proximal end of each tine 445, 447.

Figure 21:
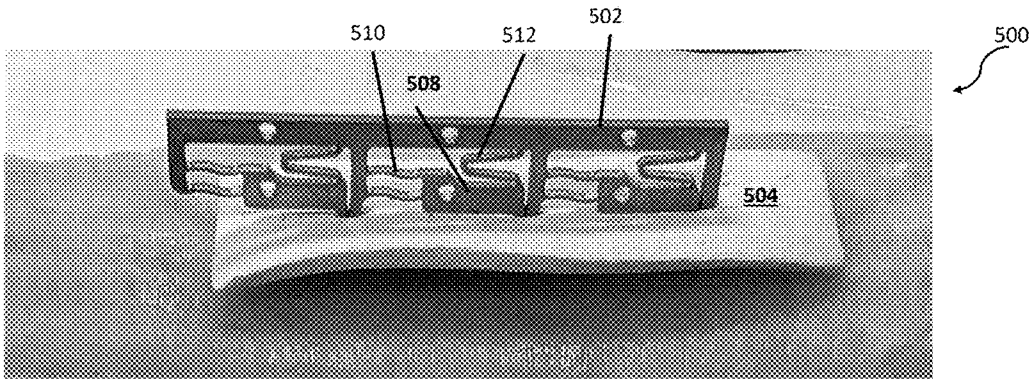
FIG. 21 is a photograph illustrating pre-compression testing a variant of the sutureless mechanically active tine connector connected to a surface of artificial tissue through a piece of polytetrafluoroethylene felt.
Figure 22:
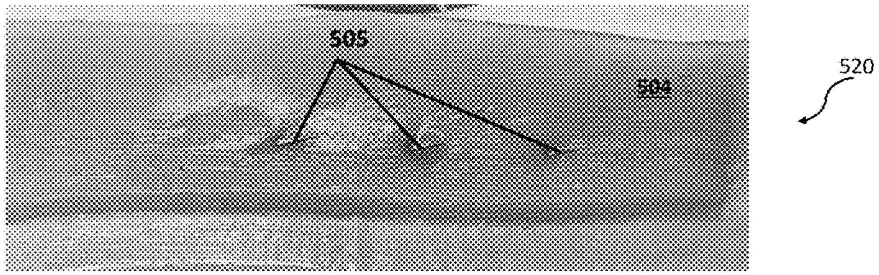
FIG. 22 is a photograph illustrating the tines passing through the opposite surface of the artificial tissue depicted in FIG. 21.

FIG. 21 illustrates attachment of representative connector variant 500, in this case connector 100, to synthetic tissue 506 through a hemostatic felt 504, such as woven polytetrafluoroethylene (PTFE), and such that the tines 505 penetrate into and through the synthetic tissue 506. Tines 505 are, however, not fully deployed as indicated the position of actuating member 508, the expansive member 512, and the stabilizing members 510. As illustrated in FIG. 21, the expansive member 512 is expanded or uncrimped and open, while the actuating member 508 is longitudinally spaced from the frame 502 of the connector 500. Further, the distal tips of the tines 505 are not compressing the synthetic tissue 506, as illustrated in FIG. 22.

Figure 23:
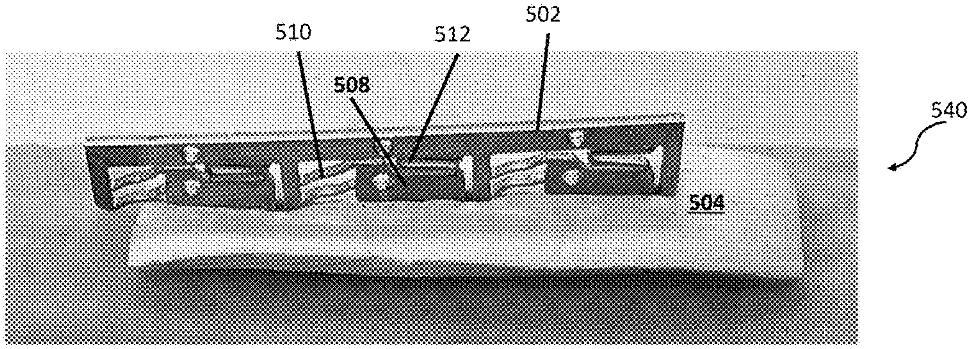
FIG. 23 is a photograph illustrating post-compression testing of the variant of the sutureless mechanically active tine connector embedded into a surface of artificial tissue through a piece of polytetrafluoroethylene felt.
Figure 24:
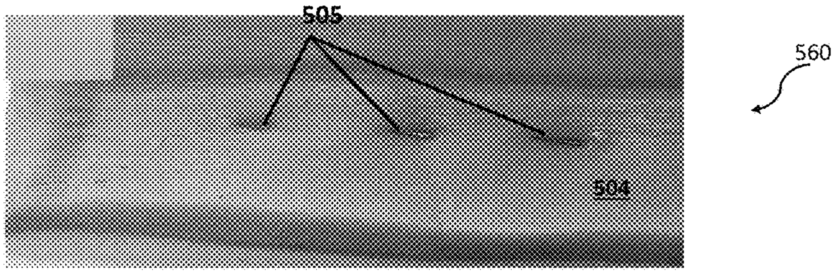
FIG. 24 is a photograph illustrating the tines fully deployed and passing through the opposite surface of the artificial tissue depicted in FIG. 23.

In contrast, FIGS. 23 and 24 illustrate connector 500 in its deployed state. FIG. 23 depicts the proximal side view 540 whereas FIG. 24 depicts the distal side view of the synthetic tissue 506. As is seen in FIGS. 23 and 24, in its deployed state, the actuating member 508 has been translated proximally toward the frame 502, the expansive members 512 are in a collapsed or compressed state, and the stabilizing members 510 have also been deformed proximally relative to frame 502. As is seen in FIG. 24, the tines 505 are compressed the distal surface of the synthetic tissue 506 such that the synthetic tissue 506 and the hemostatic felt 504 are compressed between the tines 505, the actuating member 508, and frame 502, thereby securing the synthetic tissue 506 there between.

A final set of variants of the mechanically active tine connectors of the present disclosure are presented in FIGS. 25 to 28. Common to each of the connector variants 600, 700, 800 are that they are ring structures made of plural active tine components and the ring structures are configured to and capable of everting about their central axis and allow the plural active tine components to embed in tissue. The everting nature of the ring structures of connector variants 600, 700, 800, make them particularly well suited for end-to-end anastomosis of tubular structures of anatomic or synthetic origin.

Figure 25:
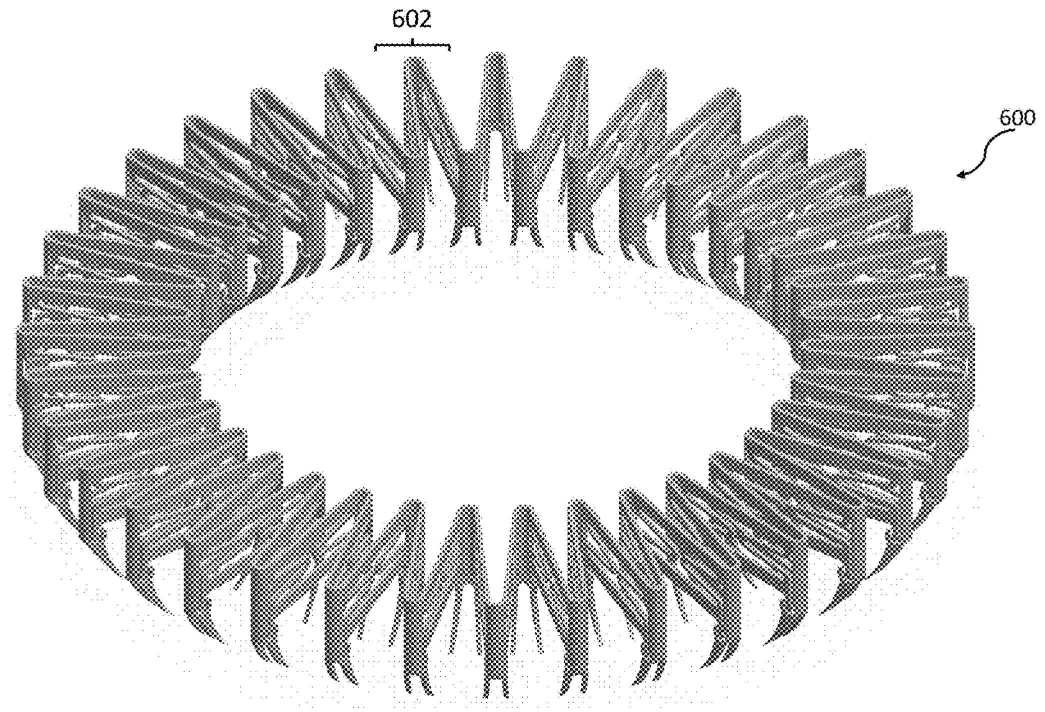
FIG. 25 is a perspective view of a mechanically active tine connector ring in accordance with the present disclosure.
Figure 26:
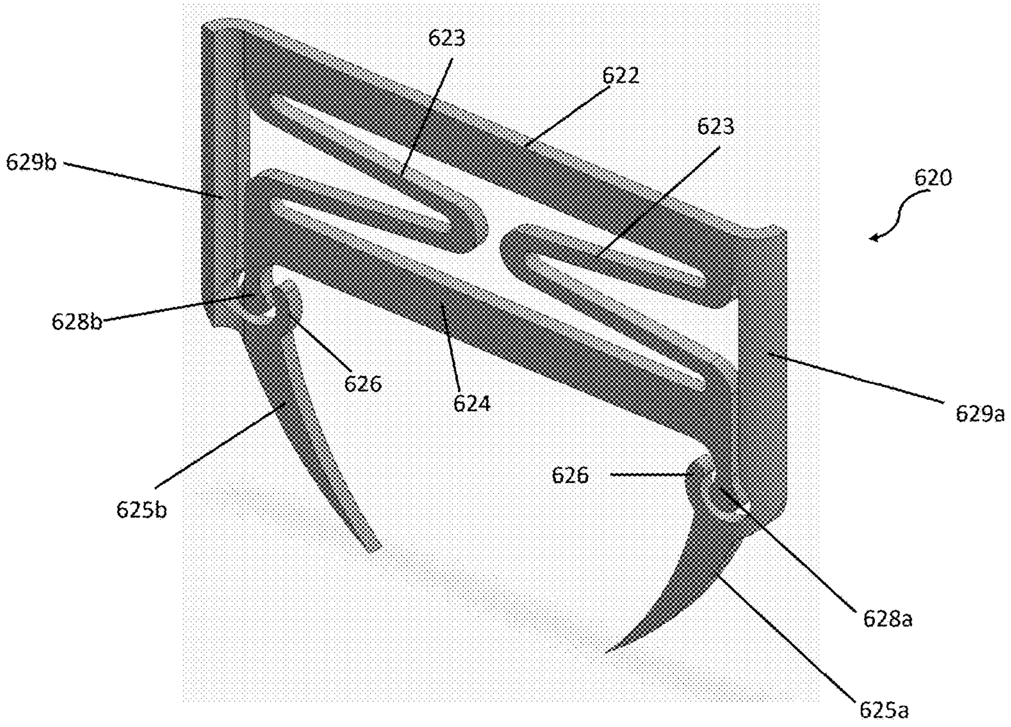
FIG. 26 is a perspective view of a single unit mechanically active tine connector of the mechanically active tine connector ring of FIG. 25.

Connector variant 600 is a ring structure composed of plural active tine assemblies 602, as illustrated in FIG. 25. An individual active tine assembly 620 is shown in FIG. 26. Each individual active tine assembly 620 may be configured in a variety of manners, including, without limitation, configuring active tine assembly 620 in a manner similar to staple-like connectors 400 420, and/or 440, described above. Alternatively, as illustrated in FIG. 26, the active tine assembly 620 may be configured to have a frame 622, with a first frame projection 629*a* and a second frame projection 629*b*. Each of the first frame projection 629*a* and second frame projection 629 join at their distal ends to a hinge region at proximal ends of each of tine 625*a* and 625*b*. The first frame projection 629*a* and second frame projection 629*b* are also joined to adjacent individual active tine assemblies 620 to form the ring structure of connector variant 620.

An actuating member 624 is provided that is joined to the frame 622 by at least one expansive member 623. The at least one expansive member 623 is configured as longitudinally expansive U-shaped or V-shaped members. It is contemplated, however, that the expansive members 623 may have any shape provided that they are capable of expanding along the longitudinal axis of the connector variant 600 as the actuating member 624 is translated along the longitudinal axis of the connector 600. While two expansive members 623 are shown in FIG. 26, the illustrated example of connector variant 600 may alternatively employ any number of expansive members 623 so long as the actuating member 624 is capable of substantially linear movement along the longitudinal axis of the connector 620.

A first actuating projection 628*a* and a second actuating projection 629*b* extend distally from opposing ends of the actuating member 624. A proximal end of each tine 625*a*, 625*b* may, optionally, be configured to receive a distal end of either the first actuating projection 628*a* or the second actuating projection 628*b* therein to allow for the first actuating projection 628*a* or the second actuating projection 628*b* to bear upon the proximal end of the respective tine 625*a*, 625*b* and exert either a tension or compression force to move the tine in a rotational manner about hinge region 627 at the juncture between each tine 625*a*, 625*b* and the first frame projection 629*a* and the second frame projection 629*b*. In this configuration, longitudinal translation of the actuating member 624 imparts either a tension or compression force to the respective tine 625*a*, 625*b* and imparts rotational movement of the respective tine about the hinge region 27 to open and/or close the position of the tines 625*a*, 625*b*.

When plural active tine assemblies 620 are joined in a ring structure, each active tine assembly 620 has a common proximal-distal orientation with other active tine assemblies 620, as illustrated in FIG. 25, and is assembled in a serpentine or zig-zag configuration into the ring structure. Optionally, the ring structure of connector 600 is capable of being everted about its central axis, with the proximal aspect of each assembly 620 being at the distal aspect of the ring structure, and the distal aspect of each assembly 620 being at the proximal aspect of the ring structure, when the connector 600 is in a pre-deployment delivery state. Upon deployment, the ring structure of connector 600 is everted about the central axis such that the frame 622 at the proximal aspect of connector 600 is oriented proximally and the tines 625*a*, 625*b* at the distal aspect of connector 600 are oriented distally.

Figure 27:
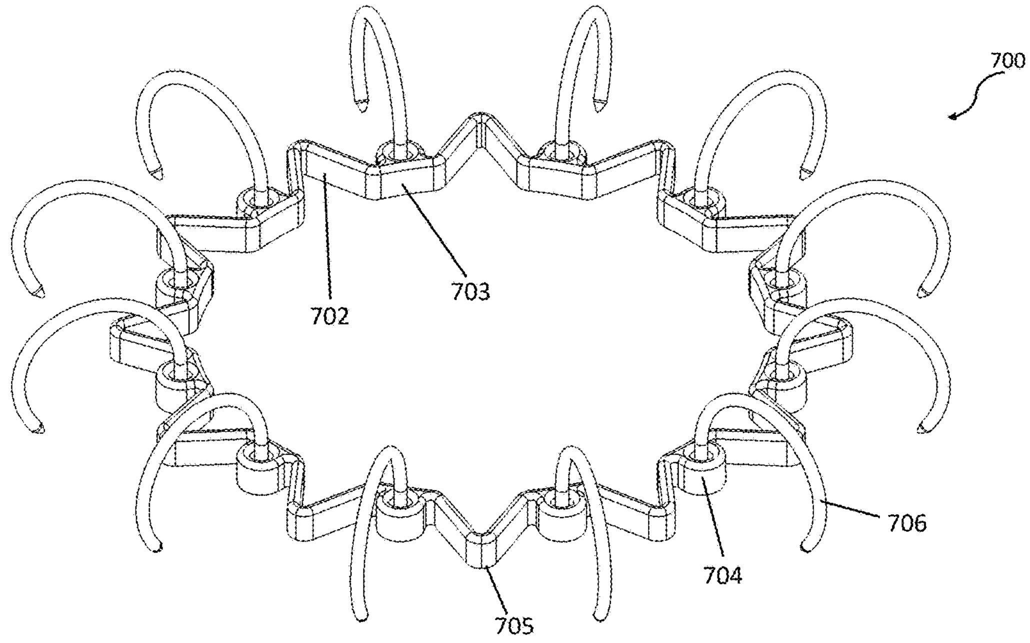
FIG. 27 is a plan view of an everting connector ring in accordance with the present disclosure.

Another variant of everting connector 700 is shown in FIG. 27. Everting connector 700 consists mainly of a serpentine frame 702 defining the ring structure, a plurality of tine seats 704 at troughs 703 of the serpentine frame 702, and a plurality of arcuate tines 706. Each of the plurality of arcuate tines 706 are coupled at a first, proximal end thereof to the tine seats 704, with a second, distal end of each of the plurality of arcuate tines 706 extending circumferentially outward and radially outwardly displaced from the peaks 705 of the serpentine frame 702. When the serpentine frame 702 is everted about its central axis, the orientation of the plurality of arcuate tines 706 and tine seats will be inverted with the second, distal ends of each of the plurality of arcuate tines 706 projecting proximally from an inner circumference of the serpentine frame 702. This everted state is particular well suited for delivery of the everting connector 700, whereas the non-everted state, depicted in FIG. 27 is the post-delivery deployed state of the everting connector 700 with the second distal ends of the tines 706 penetrating into anatomic tissue (not shown).

An advantage of everting connector 700 is that the post-delivery deployed state does not rely upon or require any pivoting or hinging of the plurality of tines 706 relative to the serpentine frame 702. Rather, the tines 706 rotate about the central axis as the everting connector 700 is deployed from its everted state to its non-everted state.

Figure 28:
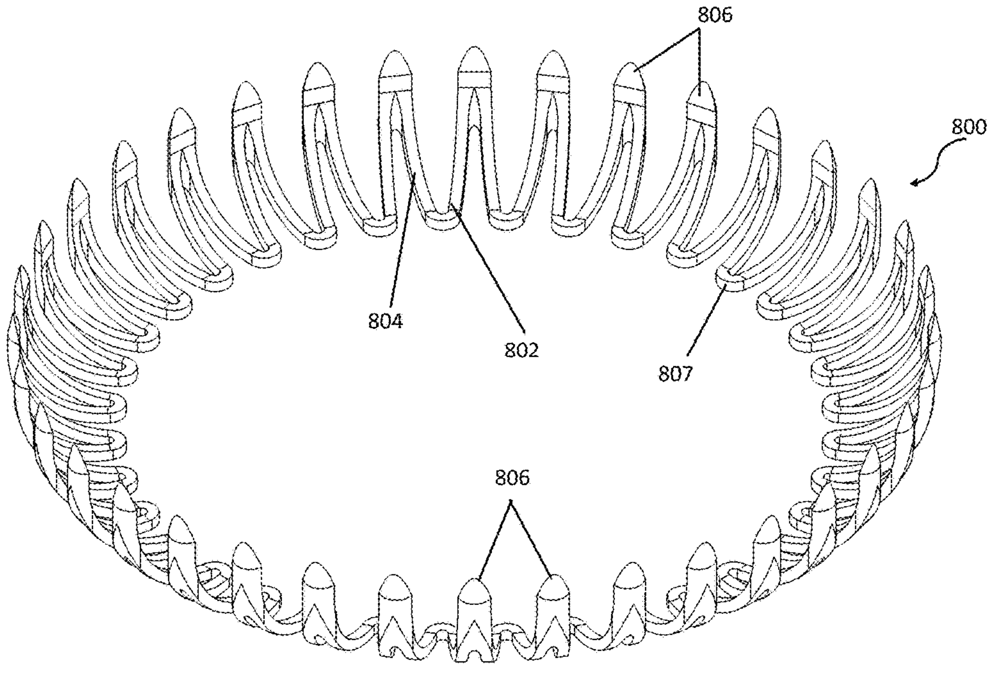
FIG. 28 is a perspective view of a variant of an everting connector ring in accordance with the present disclosure.

Another everting connector variant 800 is shown in FIG. 28. Similar to everting connector variant 700, everting connector variant 800 has a continuous serpentine frame 802 having a plurality of structural strut-like members 804 defining a plurality of peaks 805 and troughs 807. Each peak 805 is configured to have a pointed end 806 that functions in a manner similar to the tines 706, but is not a discrete component, but is integral and monolithic with the peak 805 and frame 802. The peaks 805 define an outer circumference of the everting connector variant 800 while the troughs define an inner circumference of the everting connector variant 800. The peaks 805 are formed to lie in a plane that is spaced apart from a plane defined by the plurality of troughs 807. In this manner, the continuous serpentine frame 802, the peaks 805, the troughs 807, and the pointed ends 806 define a continuous, integral ring structure without any separate movable components coupled to or attached to the everting connector 800.

When the serpentine frame 802 is everted about its central axis, the orientation of the plurality of pointed ends 806 and peaks 805 and the plurality of troughs 807 switch relative positions about the central axis of the serpentine frame 802. In this everted state, the everting connector 800 is in a delivery and pre-deployment state. By re-everting the serpentine frame, the plurality of pointed ends 806, the peaks 805, and troughs 807, the connector 800 will assume its delivered and deployed state with the pointed ends 806 embedding into anatomic tissue, not shown, about the outer circumference of the everting connector 800.

Figure 29:
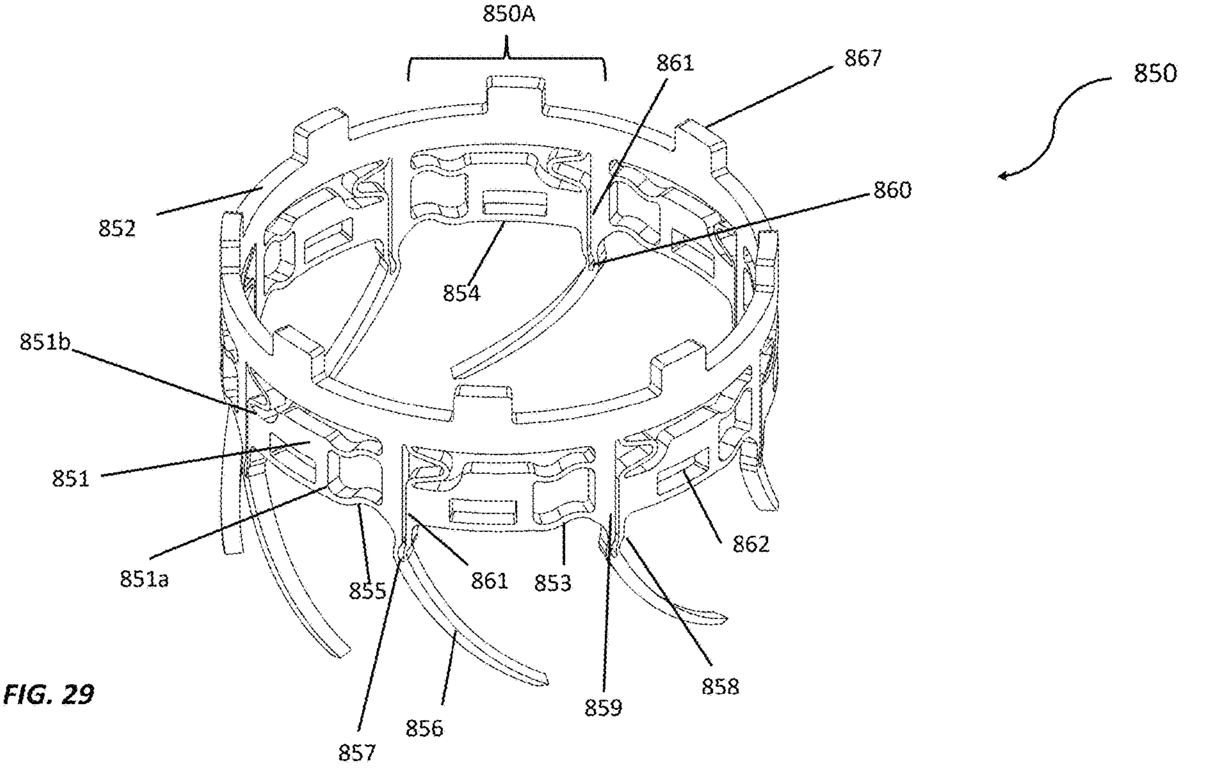
FIG. 29 is a perspective view of a single ring frame member variant of the sutureless mechanically active tine connector in accordance with the present disclosure.
Figure 30:
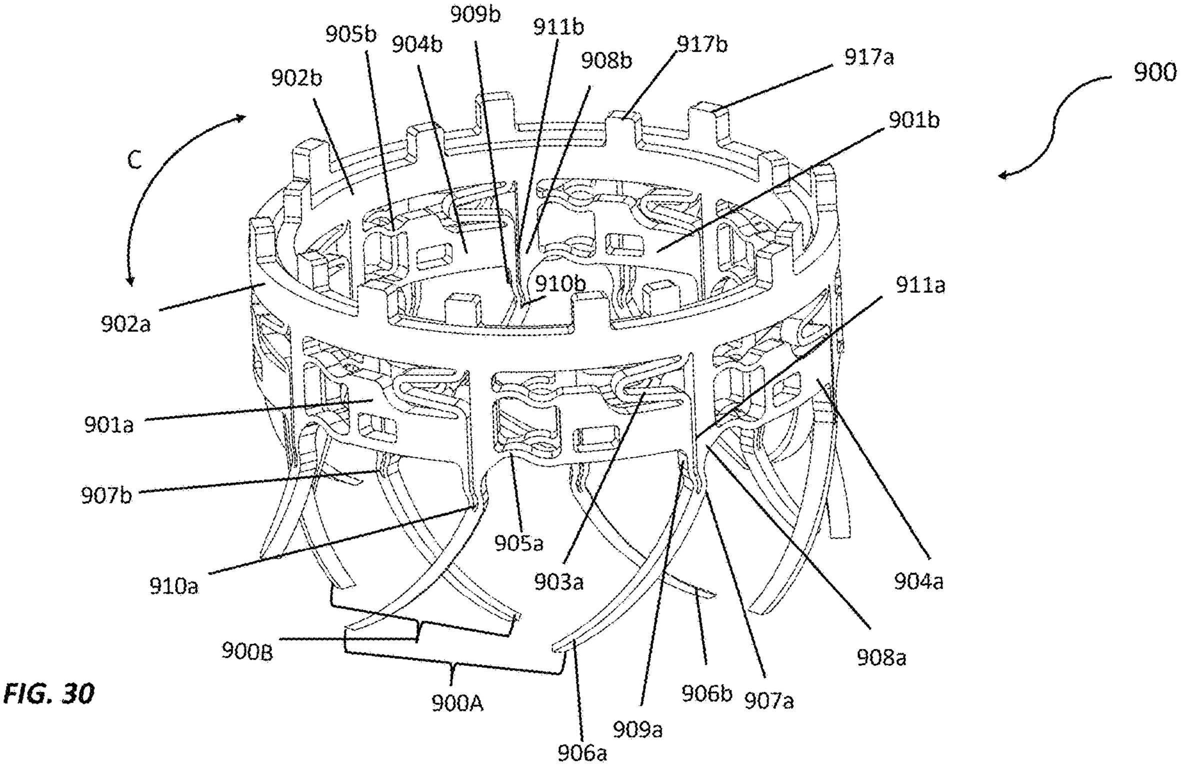
FIG. 30 is a perspective view of a dual ring frame member variant of the sutureless mechanically active tine connector in accordance with the present disclosure.

Further variants of connector 100 are illustrated in FIGS. 29 and 30. A single ring connector 850 is depicted in FIG. 29, while a dual ring connector member 900 is depicted in FIG. 30. Single ring connector 850 has a ring frame member 852 and a plurality of tine assemblies 850A arrayed about a circumference of the ring frame member 852. Optionally, the ring frame member 852 may have driver engagements 867 that are either projections from the ring frame member 852 or recesses in a proximal edge of the ring frame member 852.

Each tine assembly 850A is similar to tine assembly 100A in that it includes at least one expansive member 853, at least one actuating member 854, at least one stabilizing member 855 extending between the ring frame member 852 and the at least one actuating member 855, an optional opening 862 passing through the at least one actuating member 854, and at least one tine 856. The at least one time 856 is operably connected to both the frame 852 and to the at least one actuating member 854, and a hinge region 857 at a proximal aspect of the at least one tine 856. The at least one tine 856 is preferably tapered distally to a tapered end that assists in penetrating into anatomic tissue. A first projection 858 extends distally from the at least one actuating member 854 and is connected to the hinge region 857 of the at least one tine 856. A second projection 859 extends distally from the ring frame member 852 and is also connected to the hinge region 857 of the at least one tine 156. An opening 861 separates the first projection 858 and the second projection 859. Optionally, opening 861 terminates in a strain relief section 860 at the hinge region 857 of tine 856.

The at least one stabilizing member 855 comprises a deformable member that projects laterally on one end thereof, from the second projection 859 extending from ring frame member 852. At an opposite end of the at least one stabilizing member 855, the at least one stabilizing member 855 connects with a first portion 851*a* of a main body 851 of the actuating member 854. Thus, the at least one stabilizing member 855 extends between the second projection 859 and the main body 851 and joins the first portion 851*a* of the main body 851. The at least one stabilizing member 851 may be linear, curvilinear, or have simple or complex curves along its length.

At a second portion 851*b* of the main body 851, the at least one expansive member 853 connects to the main body 851 and the ring frame member 852. The first portion of the main body 851*a* and the second portion of the main body 851*b* are preferably located at opposite aspects of the main body 851. In this manner, translation of the main body 851 along a longitudinal axis of the connector 850, either proximally or distally relative to the ring frame member 852, is stabilized by the at least one stabilizing member 855 and the expansive member 853. This arrangement stabilizes the main body 851 and allows the longitudinal translation of both the first portion 851*a* and the second portion 851*b* of the main body to move substantially simultaneously and evenly along the longitudinal axis L while maintaining a substantial parallel relationship relative to the circumferential axis of the ring frame member 850. Further, in this manner, the main body exerts a linear force to the first projection 858 that is substantially parallel to the longitudinal axis of the connector 850. The linear force exerted by the first projection 858 acts at the hinge region 857 to deflect the tine 856. In this manner, either proximal or distal movement of the main body 851 of the actuating member 854 deflects the tine 856 either proximally or distally, respectively.

As indicated above, the first projection 858 and the second projection 859 are configured to carry compression and/or tension forces as the at least one actuating member 854 is moved proximally and or distally relative to the ring frame member 852 and rotates the at least one tine 856 either proximally or distally about the hinge region 857.

The dual ring connector 900, illustrated in FIG. 30, consists generally of two concentric single ring connectors 850 operably coupled to each other and independently rotatable relative to each other. Dual ring connector 900 includes a first ring frame member 902*a* and a second ring frame member 902*b* concentrically disposed relative to one another. A guide (not shown) is provided between the first ring frame member 902*a* and the second ring member 902*b* to facilitate independent rotation of the first ring frame member 902*a* relative to the second ring member 902*b* about a common circumferential axis C. Each of the first ring member 902*a* and the second ring member 902*b* have common elements associated therewith and differ primarily in the helical orientation of the plurality of tines 906*a*, 906*b*, respectively. Specifically, the plurality of tines 906*a* and 906*b* associated with first ring member 902*a* and second ring member 902*b*, respectively, have opposite helical orientations. It will be appreciated by those skilled in the art that this opposite helical orientation facilitates greater penetration into anatomic tissue and/or non-anatomic devices, as well as provides greater resistance to pull-out from the anatomic tissue and/or non-anatomic tissue.

Each of the first ring member 902*a* and the second ring member 902*b* has a plurality of driver engagements 917*a*, 917*b* that are either projections from or recesses in a proximal aspect of the first ring member 902*a*, 902*b*, respectively. Similarly, each of the first ring member 902*a* and the second ring member 902*b* has a plurality of tine assemblies 900A, 900B, respectively, projecting distally therefrom. Each of the plurality of tine assemblies 900A, 900B have at least one expansive member 903*a, b*, at least one actuating member 904*a*, 904*b*, at least one stabilizing member 905*a*, 905*b* extending between a respective ring frame member 902*a*, 902*b* and the at least one actuating member 905*a*, 905*b*, an optional opening passing through the at least one actuating member 904*a*, 904*b*, and at least one tine 906*a*, 906*b*. The at least one tine 906*a*, 906*b* is operably connected to both the ring frame member 902*a*, 902*b* and to the at least one actuating member 904*a*, 904*b*, and a hinge region 907*a*, 907*b* at a proximal aspect of the at least one tine 906*a*, 906*b*. The at least one tine 906*a*, 906*b* is preferably tapered distally to a tapered end that assists in penetrating into anatomic tissue or a non-anatomic device. A first projection 908*a*, 908*b* extends distally from the at least one actuating member 904*a*, 904*b* and is connected to the hinge region 907*a*, 907*b* of the at least one tine 906*a*, 906*b*. A second projection 909*a*, 909*b* extends distally from its respective ring frame member 902*a*, 902*b* and is also connected to the hinge region 907*a*, 907*b* of the respective at least one tine 906*a*, 906*b*. An opening 911*a*, 911*b* separates each first projection 908*a*, 908*b* from an adjacent second projection 909*a*, 909*b*. Optionally, opening 911*a*, 911*b* terminates in a strain relief section 910*a*, 910*b* at the hinge region 907*a*, 907*b* of the associated tine 906*a*, 906*b*.

The at least one stabilizing member 905*a*, 905*b* comprises a deformable member that projects laterally on one end thereof, from the second projection 909*a*, 909*b* extending from ring frame member 902*a*, 902*b*. At an opposite end of the at least one stabilizing member 905*a*, 905*b*, it joins with a first portion of a main body 901*a*, 901*b* of the actuating member 904*a*, 904*b*. Thus, the at least one stabilizing member 905*a*, 905*b* extends between the second projection 909*a*, 909*b* and the main body 901*a*, 901*b* and joins the first portion of the main body 901*a*, 901*b*. The at least one stabilizing member 901*a*, 901*b* may be linear, curvilinear, or have simple or complex curves along its length.

The at least one expansive member 903*a*, 903*b* connects to the main body 901*a*, 901*b* of the actuating member 904*a*, 904*b* and the ring frame member 902*a*, 902*b*. The first portion of the main body and the second portion of the main body are preferably located at opposite aspects of the main body 901*a*, 901*b*. In this manner, translation of the main body 901*a*, 901*b* along a longitudinal axis of the connector 900, either proximally or distally relative to the ring frame member 902*a*, 902*b*, is stabilized by the at least one stabilizing member 905*a*, 905*b* and the expansive member 903*a*, 903*b*. This arrangement stabilizes the main body 901*a*, 901*b* and allows the longitudinal translation of both the first portion and the second portion of the main body 901*a*, 901*b* to move substantially simultaneously and evenly along the longitudinal axis L while maintaining a substantial parallel relationship relative to the circumferential axis C of the dual ring connector 900. Further, in this manner, movement of the main body 901*a*, 901*b* exerts a linear force to the first projection 908*a*, 908*b* that is substantially parallel to the longitudinal axis of the connector 850. The linear force exerted by the first projection 908*a*, 908*b* acts at the respective hinge region 907*a*, 907*b* to deflect the associated tine 906*a*, 906*b*, which each, in turn, rotate in opposite directions about their hinge regions 907*a*, 907*b* given their opposite helical orientations. In this manner, either proximal or distal movement of the main body 901*a*, 901*b* of the actuating member 904*a*, 904*b* deflects the tines 906*a*, 906*b* either proximally or distally, respectively, in their opposite circumferential orientations about circumferential axis C.

The foregoing described variants of connector 100, 120, 140, 160, 180, 200, 220, 240, 260, 280, 300, 320, 340, 360, 380, 850, and/or 900, including the staple-like connectors 400, 420, 440, and the everting connectors 600, 700, 800 are provided as examples of the disclosed connectors useful for end-to-side and/or end-to-end anastomosis of tubular structures of anatomic or synthetic origin. It is expressly intended that the illustrated and described variants of the connectors of the present disclosure that aspects and component parts and structures of the various variants may be interchanged or be made interchangeable among the different variants so as not to limit the scope of the disclosure to the illustrated and described variants. For example, the barb 287 on tine 286 depicted in FIG. 12 may be employed on any of the illustrated and described tines across all variants of the present disclosure. Similarly, the different illustrated configurations and conformations of the actuating members may be used with different variants of the present disclosure. Accordingly, the scope of the present disclosure is intended to be limited only by the appended claims taken in view of the illustrated and described exemplary variants.

Those of skill in the art will understand and appreciate that modifications may be made to the above description and still remain within the scope of the disclosure. For example, with respect to all disclosed variants of the sutureless connectors, the frame may be a linear structure, a ring structure, a tubular structure, a curvilinear structure, such as a generally sinusoidal shape, a zig-zag shape, or the like, the tines may be curved, linear, tapered, or untampered, the actuating member may have a wide variety of shapes including generally rectangular, square, oval, elliptical, or other polygonal shapes, and stabilizing members may have one, two, three or more arms, be curved, linear, sinusoidal, or zig-zag shaped, or the like.

The size of the connector device may cover a wide range and may depend on the type of procedure it is adapted for. This may include larger dimensions for more robust procedures in more open spaces and smaller dimensions for more delicate procedures in more constrained spaces. The material of the device may be adapted based on the flexibility or rigidity appropriate for a given type of use. Any combination of these modifications may be included and considered with one another for providing a suitable instrument.

Although the present invention has been described with reference to preferred variants, persons skilled in the art will recognize that changes may be made in form and detail without departing from the spirit and scope of the invention.

The invention claimed is:

1. A method for making a fluid coupling to an anatomical structure, comprising the steps of:

a. positioning a frame member having a plurality of tines projecting distally from the frame against an outer wall surface of the anatomic structure, the anatomic structure having an inner wall and an outer wall;

b. penetrating the plurality of tines into and past the inner wall of the anatomic structure;

c. actuating the plurality of tines to bear against the inner wall of the anatomic structure by axially compressing the frame against the outer wall of the anatomic structure, wherein the axial compression deforms a portion of the frame.

2. The method of claim 1, wherein the step of positioning the frame member further comprises the step of providing a frame member having a ring structure and the plurality tines project helically from a distal surface of the ring structure.

3. The method of claim 2, wherein the step of positioning the frame member further comprises the step of providing a frame member having a frame member having one of a frame tension member or a frame compression member projecting therefrom; at least one actuating member connected to the frame member by a stabilizing member and one of an actuating tension member or an actuating compression member and movable relative to the frame member in a substantially co-planar manner; at least one tine coupled to one of a frame tension member or a frame compression member and one of an actuating tension member or an actuating compression member, whereby axial movement of the frame member relative to the at least one actuating member imparts movement to the at least one tine; and a tubular conduit coupled to the frame member and projecting proximally from the frame member.

4. The method of claim 3, wherein the step of actuating the plurality of tines further comprises the step of creating a hemostatic fluid flow coupling between the tubular conduit and the anatomic structure.

5. The method of claim 1, wherein the actuating step further comprises the step of stabilizing an actuating member coupled to the frame member and to the plurality of tines.

6. The method of claim 5, wherein the step of actuating the plurality of tines further comprises the step of applying a compressive force to the ring member.

7. The method of claim 5, wherein the step of actuating the plurality of tines further comprises the step of stabilizing the actuating member such that the actuating member translates along a longitudinal axis of the ring frame member.

8. The method of claim 7, wherein the step of stabilizing the actuating member further includes the step of maintaining the actuating member substantially parallel to a circumferential axis of the ring structure.

9. A method for making a fluid coupling to an anatomical structure having an inner wall and outer wall thereof, comprising the steps of:

a. positioning a frame member comprising a ring structure against the outer wall of the anatomical structure, the ring structure being comprised of a plurality of tine assemblies, each of the plurality of tine assemblies comprising a frame tension member and a frame compression member projecting distally from the ring structure therefrom, at least one actuating member connected to the frame member by a stabilizing member and one of an actuating tension member or an actuating compression member and movable relative to the frame member, each of the plurality of tines being coupled to one of the frame tension member and the frame compression member and one of an actuating tension member or an actuating compression member, whereby axial movement of the at least one actuating member relative to the frame imparts movement to the at least one tine and the ring structure; and a tubular conduit coupled to an inner wall of the ring structure and projecting proximally from the ring structure;

b. penetrating the plurality of tines into and past the inner wall of the anatomic structure;

c. actuating the plurality of tines to bear against the inner wall of the anatomic structure and axially compress the ring structure against the outer wall of the anatomic structure and create a hemostatic fluid flow coupling between the frame member and the anatomical structure.

10. The method of claim 9, wherein the plurality tines project helically from a distal surface of the ring structure.

11. The method of claim 9, wherein the actuating step further comprises the step of stabilizing the at least one actuating member coupled to the ring frame member and to the plurality of tines.

12. The method of claim 11, further comprising the steps of applying a compressive force to the ring member and actuating the actuating member.

13. The method of claim 12, the step of actuating the actuating member further comprises the step of stabilizing the actuating member.

14. The method of claim 13, wherein the step of stabilizing the actuating member further includes the step of maintaining the actuating member substantially parallel to a circumferential axis of the ring structure.

* * * * *